US009622675B2

(12) United States Patent
Leyde et al.

(10) Patent No.: US 9,622,675 B2
(45) Date of Patent: Apr. 18, 2017

(54) COMMUNICATION ERROR ALERTING IN AN EPILEPSY MONITORING SYSTEM

(75) Inventors: Kent W. Leyde, Sammamish, WA (US); John F. Harris, Bellevue, WA (US)

(73) Assignee: CYBERONICS, INC., Houston, TX (US)

(*) Notice: Subject to any disclaimer, the term of this patent is extended or adjusted under 35 U.S.C. 154(b) by 908 days.

(21) Appl. No.: 13/070,333

(22) Filed: Mar. 23, 2011

(65) Prior Publication Data

US 2011/0213222 A1 Sep. 1, 2011

Related U.S. Application Data

(63) Continuation of application No. 12/020,507, filed on Jan. 25, 2008.

(Continued)

(51) Int. Cl.
*A61B 5/00* (2006.01)
*A61B 5/04* (2006.01)
(Continued)

(52) U.S. Cl.
CPC .......... *A61B 5/0476* (2013.01); *A61B 5/0006* (2013.01); *A61B 5/0031* (2013.01);
(Continued)

(58) Field of Classification Search
CPC ... A61B 5/0006; A61B 5/0031; A61B 5/0476; A61B 5/4094; A61B 2560/0271;
(Continued)

(56) References Cited

U.S. PATENT DOCUMENTS 3,218,638 A 11/1965 Honig
3,498,287 A 3/1970 Ertl
(Continued)

FOREIGN PATENT DOCUMENTS

CA 2251852 4/1999
CA 2423840 2/2002
(Continued)

OTHER PUBLICATIONS

Leyde et al.; U.S. Appl. No. 13/441,609 entitled "Multi-Channel Amplifier Techniques," filed Apr. 6, 2012.
(Continued)

*Primary Examiner* — Christine H Matthews
*Assistant Examiner* — Joshua D Lannu
(74) *Attorney, Agent, or Firm* — Foley & Lardner LLP

(57) ABSTRACT

Systems and methods for monitoring neurological signals in a patient are provided. The system includes: an implantable sensor adapted to collect neurological signals; an implantable assembly configured to sample the neurological signals collected by the sensor; and a rechargeable communication device external to the patient's body, said communication device configured to wirelessly communicate with the implantable assembly and to transmit a communication error alert to a caregiver advisory device in the event of a communication error between the implantable assembly and the communication device.

32 Claims, 17 Drawing Sheets

Related U.S. Application Data

(60) Provisional application No. 60/897,551, filed on Jan. 25, 2007.

(51) Int. Cl.
*A61B 5/0476* (2006.01)
*A61M 5/142* (2006.01)
*A61N 1/36* (2006.01)
*A61N 1/372* (2006.01)
*G06F 19/00* (2011.01)

(52) U.S. Cl.
CPC .... *A61B 5/4094* (2013.01); *A61B 2560/0271* (2013.01); *A61M 5/14276* (2013.01); *A61N 1/36082* (2013.01); *A61N 1/37247* (2013.01); *A61N 1/37258* (2013.01); *A61N 1/37282* (2013.01); *G06F 19/3418* (2013.01)

(58) Field of Classification Search
CPC ........... A61M 5/14276; A61N 1/36082; A61N 1/37247; A61N 1/37258; A61N 1/37282; G06F 19/3418
See application file for complete search history.

(56) References Cited

U.S. PATENT DOCUMENTS

| | | |
|---|---|---|
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,934,372 A | 6/1990 | Corenman et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deCorolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A | 5/1996 | Prammer |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |

(56) References Cited

U.S. PATENT DOCUMENTS

| | | |
|---|---|---|
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,782,891 A | 7/1998 | Hassler et al. |
| 5,792,186 A | 8/1998 | Rise |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,938,689 A | 8/1999 | Fischell et al. |
| 5,941,906 A | 8/1999 | Barreras et al. |
| 5,950,632 A | 9/1999 | Reber et al. |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,108,571 A * | 8/2000 | Minoz et al. ................ 600/361 |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Quyen et al. |
| 6,443,890 B1 * | 9/2002 | Schulze ............... A61B 5/0002 128/903 |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,594,524 B2 * | 7/2003 | Esteller et al. ................ 607/45 |
| 6,597,954 B1 | 7/2003 | Pless et al. |
| 6,600,956 B2 | 7/2003 | Maschino |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,819,956 B2 | 11/2004 | DiLorenzo |
| 6,879,859 B1 | 4/2005 | Boveja |

(56) References Cited

U.S. PATENT DOCUMENTS

| | | | |
|---|---|---|---|
| 6,893,395 B1 | 5/2005 | Kraus et al. | |
| 6,901,294 B1 | 5/2005 | Whitehurst et al. | |
| 6,901,296 B1 | 5/2005 | Whitehurst et al. | |
| 6,912,419 B2 | 6/2005 | Hill | |
| 6,921,538 B2 | 7/2005 | Donovan | |
| 6,921,541 B2 | 7/2005 | Chasin et al. | |
| 6,923,784 B2 | 8/2005 | Stein | |
| 6,931,274 B2 | 8/2005 | Williams | |
| 6,934,580 B1 | 8/2005 | Osorio | |
| 6,937,891 B2 | 8/2005 | Leinders et al. | |
| 6,944,501 B1 | 9/2005 | Pless | |
| 6,950,706 B2 | 9/2005 | Rodriguez | |
| 6,973,342 B1 | 12/2005 | Swanson | |
| 6,990,372 B2 | 1/2006 | Perron et al. | |
| 7,010,351 B2 | 3/2006 | Firlik et al. | |
| 7,089,059 B1 | 8/2006 | Pless | |
| 7,117,108 B2 | 10/2006 | Rapp et al. | |
| 7,174,212 B1 | 2/2007 | Klehn et al. | |
| 7,177,701 B1 | 2/2007 | Pianca | |
| 7,209,787 B2 | 4/2007 | DiLorenzo | |
| 7,212,851 B2 | 5/2007 | Donoghue et al. | |
| 7,231,254 B2 | 6/2007 | DiLorenzo | |
| 7,242,984 B2 | 7/2007 | DiLorenzo | |
| 7,277,758 B2 | 10/2007 | DiLorenzo | |
| 7,294,105 B1 * | 11/2007 | Islam | A61B 5/0006 128/903 |
| 7,324,851 B1 | 1/2008 | DiLorenzo | |
| 7,373,198 B2 | 5/2008 | Bibian et al. | |
| 7,403,820 B2 | 7/2008 | DiLorenzo | |
| 7,463,917 B2 | 12/2008 | Martinez | |
| 7,483,743 B2 * | 1/2009 | Mann et al. | 607/17 |
| 7,623,928 B2 | 11/2009 | DiLorenzo | |
| 7,631,015 B2 | 12/2009 | Gupta et al. | |
| 7,747,325 B2 | 6/2010 | Dilorenzo | |
| 7,805,196 B2 | 9/2010 | Miesel et al. | |
| 7,881,798 B2 | 2/2011 | Miesel et al. | |
| 8,055,348 B2 | 11/2011 | Heruth et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0035338 A1 | 3/2002 | Dear et al. | |
| 2002/0054694 A1 | 5/2002 | Vachtsevanos et al. | |
| 2002/0072770 A1 | 6/2002 | Pless | |
| 2002/0072776 A1 | 6/2002 | Osorio et al. | |
| 2002/0072782 A1 | 6/2002 | Osorio et al. | |
| 2002/0077670 A1 | 6/2002 | Archer et al. | |
| 2002/0095099 A1 | 7/2002 | Quyen et al. | |
| 2002/0099412 A1 | 7/2002 | Fischell et al. | |
| 2002/0103512 A1 | 8/2002 | Echauz et al. | |
| 2002/0109621 A1 | 8/2002 | Khair et al. | |
| 2002/0111542 A1 | 8/2002 | Warkentin et al. | |
| 2002/0116042 A1 | 8/2002 | Boling | |
| 2002/0126036 A1 | 9/2002 | Flaherty et al. | |
| 2002/0147388 A1 | 10/2002 | Mass et al. | |
| 2002/0169485 A1 | 11/2002 | Pless et al. | |
| 2003/0004428 A1 | 1/2003 | Pless | |
| 2003/0009207 A1 | 1/2003 | Paspa et al. | |
| 2003/0013981 A1 | 1/2003 | Gevins et al. | |
| 2003/0018367 A1 | 1/2003 | DiLorenzo | |
| 2003/0028072 A1 | 2/2003 | Fischell et al. | |
| 2003/0050549 A1 | 3/2003 | Sochor | |
| 2003/0050730 A1 | 3/2003 | Greeven et al. | |
| 2003/0073917 A1 | 4/2003 | Echauz et al. | |
| 2003/0074033 A1 | 4/2003 | Pless et al. | |
| 2003/0083716 A1 | 5/2003 | Nicolelis et al. | |
| 2003/0114886 A1 | 6/2003 | Gluckman et al. | |
| 2003/0144709 A1 | 7/2003 | Zabara et al. | |
| 2003/0144711 A1 | 7/2003 | Pless et al. | |
| 2003/0144829 A1 | 7/2003 | Geatz et al. | |
| 2003/0149457 A1 | 8/2003 | Tcheng et al. | |
| 2003/0158587 A1 | 8/2003 | Esteller et al. | |
| 2003/0167078 A1 | 9/2003 | Weisner et al. | |
| 2003/0174554 A1 | 9/2003 | Dunstone et al. | |
| 2003/0176806 A1 | 9/2003 | Pineda et al. | |
| 2003/0187621 A1 | 10/2003 | Nikitin et al. | |
| 2003/0195574 A1 | 10/2003 | Osorio et al. | |
| 2003/0195588 A1 | 10/2003 | Fischell et al. | |
| 2003/0195602 A1 | 10/2003 | Boling | |
| 2004/0034368 A1 | 2/2004 | Pless et al. | |
| 2004/0039427 A1 | 2/2004 | Barrett et al. | |
| 2004/0039981 A1 | 2/2004 | Riedl et al. | |
| 2004/0054297 A1 | 3/2004 | Wingeier et al. | |
| 2004/0059761 A1 | 3/2004 | Hively | |
| 2004/0068199 A1 | 4/2004 | Echauz et al. | |
| 2004/0073273 A1 | 4/2004 | Gluckman et al. | |
| 2004/0077995 A1 | 4/2004 | Ferek-Petric | |
| 2004/0078160 A1 | 4/2004 | Frei et al. | |
| 2004/0082984 A1 | 4/2004 | Osorio et al. | |
| 2004/0087835 A1 | 5/2004 | Hively | |
| 2004/0097802 A1 | 5/2004 | Cohen | |
| 2004/0122281 A1 | 6/2004 | Fischell et al. | |
| 2004/0122335 A1 | 6/2004 | Sackellares et al. | |
| 2004/0122488 A1 * | 6/2004 | Mazar et al. | 607/60 |
| 2004/0127810 A1 | 7/2004 | Sackellares et al. | |
| 2004/0133119 A1 | 7/2004 | Osorio et al. | |
| 2004/0133248 A1 | 7/2004 | Frei et al. | |
| 2004/0133390 A1 | 7/2004 | Osorio et al. | |
| 2004/0138516 A1 | 7/2004 | Osorio et al. | |
| 2004/0138517 A1 | 7/2004 | Osorio et al. | |
| 2004/0138536 A1 | 7/2004 | Frei et al. | |
| 2004/0138578 A1 | 7/2004 | Pineda et al. | |
| 2004/0138579 A1 | 7/2004 | Deadwyler et al. | |
| 2004/0138580 A1 | 7/2004 | Frei et al. | |
| 2004/0138581 A1 | 7/2004 | Frei et al. | |
| 2004/0138647 A1 | 7/2004 | Osorio et al. | |
| 2004/0138711 A1 | 7/2004 | Osorio et al. | |
| 2004/0138721 A1 | 7/2004 | Osorio et al. | |
| 2004/0147969 A1 | 7/2004 | Mann et al. | |
| 2004/0152958 A1 | 8/2004 | Frei et al. | |
| 2004/0153129 A1 | 8/2004 | Pless et al. | |
| 2004/0158119 A1 | 8/2004 | Osorio et al. | |
| 2004/0172089 A1 | 9/2004 | Whitehurst et al. | |
| 2004/0176359 A1 | 9/2004 | Wermeling | |
| 2004/0181263 A1 | 9/2004 | Balzer et al. | |
| 2004/0199212 A1 | 10/2004 | Fischell | |
| 2004/0210269 A1 | 10/2004 | Shalev et al. | |
| 2004/0243146 A1 | 12/2004 | Chesbrough et al. | |
| 2004/0267152 A1 | 12/2004 | Pineda et al. | |
| 2005/0004621 A1 | 1/2005 | Boveja et al. | |
| 2005/0010113 A1 | 1/2005 | Hall et al. | |
| 2005/0010261 A1 | 1/2005 | Luders et al. | |
| 2005/0015128 A1 | 1/2005 | Rezai et al. | |
| 2005/0015129 A1 | 1/2005 | Mische | |
| 2005/0021105 A1 | 1/2005 | Firlik et al. | |
| 2005/0021108 A1 | 1/2005 | Klosterman et al. | |
| 2005/0021313 A1 | 1/2005 | Nikitin et al. | |
| 2005/0027328 A1 | 2/2005 | Greenstein | |
| 2005/0033369 A1 | 2/2005 | Badelt | |
| 2005/0043772 A1 | 2/2005 | Stahmann et al. | |
| 2005/0043774 A1 | 2/2005 | Devlin et al. | |
| 2005/0049649 A1 | 3/2005 | Luders et al. | |
| 2005/0059867 A1 | 3/2005 | Cheng | |
| 2005/0070970 A1 | 3/2005 | Knudson et al. | |
| 2005/0075067 A1 | 4/2005 | Lawson et al. | |
| 2005/0096710 A1 | 5/2005 | Kieval | |
| 2005/0113885 A1 | 5/2005 | Haubrich et al. | |
| 2005/0124863 A1 | 6/2005 | Cook | |
| 2005/0131493 A1 | 6/2005 | Boveja et al. | |
| 2005/0137640 A1 | 6/2005 | Freeberg et al. | |
| 2005/0143786 A1 | 6/2005 | Boveja | |
| 2005/0143787 A1 | 6/2005 | Boveja et al. | |
| 2005/0149123 A1 | 7/2005 | Lesser et al. | |
| 2005/0182308 A1 | 8/2005 | Bardy | |
| 2005/0182464 A1 | 8/2005 | Schulte et al. | |
| 2005/0187789 A1 | 8/2005 | Hatlestad | |
| 2005/0197590 A1 | 9/2005 | Osorio et al. | |
| 2005/0203366 A1 | 9/2005 | Donoghue et al. | |
| 2005/0203584 A1 | 9/2005 | Twetan et al. | |
| 2005/0209218 A1 | 9/2005 | Meyerson et al. | |
| 2005/0222503 A1 | 10/2005 | Dunlop et al. | |
| 2005/0222641 A1 | 10/2005 | Pless | |
| 2005/0228249 A1 | 10/2005 | Boling | |
| 2005/0228461 A1 | 10/2005 | Osorio et al. | |
| 2005/0231374 A1 | 10/2005 | Diem et al. | |

(56) References Cited

U.S. PATENT DOCUMENTS

| | | |
|---|---|---|
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0136006 A1 | 6/2006 | Giftakis et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0253096 A1 | 11/2006 | Blakley et al. |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027514 A1 | 2/2007 | Gerber |
| 2007/0035910 A1 | 2/2007 | Stevenson |
| 2007/0043459 A1 | 2/2007 | Abbott, III et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0149952 A1 | 6/2007 | Bland et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0185890 A1 | 8/2007 | VanEpps et al. |
| 2007/0197878 A1 | 8/2007 | Shklarski |
| 2007/0213629 A1 | 9/2007 | Greene |
| 2007/0213785 A1 | 9/2007 | Osorio et al. |
| 2007/0217121 A1 | 9/2007 | Fu et al. |
| 2007/0238939 A1 | 10/2007 | Giftakis et al. |
| 2007/0244407 A1 | 10/2007 | Osorio |
| 2007/0250077 A1 | 10/2007 | Skakoon et al. |
| 2007/0250901 A1 | 10/2007 | McIntire et al. |
| 2007/0287931 A1 | 12/2007 | DiLorenzo |
| 2007/0293774 A1 | 12/2007 | Acquista |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0082019 A1 | 4/2008 | Ludving et al. |
| 2008/0091090 A1 | 4/2008 | Guillory et al. |
| 2008/0103556 A1 | 5/2008 | Li et al. |
| 2008/0114417 A1 | 5/2008 | Leyde |
| 2008/0119900 A1 | 5/2008 | DiLorenzo |
| 2008/0161712 A1 | 7/2008 | Leyde |
| 2008/0161713 A1 | 7/2008 | Leyde et al. |
| 2008/0183057 A1 | 7/2008 | Taube |
| 2008/0183096 A1 | 7/2008 | Snyder et al. |
| 2008/0183097 A1 | 7/2008 | Leyde et al. |
| 2008/0208074 A1 | 8/2008 | Snyder et al. |
| 2008/0221876 A1 | 9/2008 | Holdrich |
| 2008/0234598 A1 | 9/2008 | Snyder et al. |
| 2008/0255582 A1 | 10/2008 | Harris |
| 2008/0273287 A1 | 11/2008 | Iyer et al. |
| 2008/0288023 A1* | 11/2008 | John ............... A61N 1/37247 607/59 |
| 2008/0319281 A1 | 12/2008 | Aarts |
| 2009/0018609 A1 | 1/2009 | DiLorenzo |
| 2009/0062682 A1 | 3/2009 | Bland et al. |
| 2009/0062696 A1 | 3/2009 | Nathan et al. |
| 2009/0171168 A1 | 7/2009 | Leyde et al. |
| 2009/0171420 A1 | 7/2009 | Brown et al. |
| 2009/0264952 A1 | 10/2009 | Jassemidis et al. |
| 2010/0023089 A1 | 1/2010 | DiLorenzo |
| 2010/0125219 A1 | 5/2010 | Harris et al. |
| 2010/0145176 A1 | 6/2010 | Himes |
| 2010/0168603 A1 | 7/2010 | Himes et al. |
| 2010/0168604 A1 | 7/2010 | Echauz et al. |
| 2010/0179627 A1 | 7/2010 | Floyd et al. |
| 2010/0217348 A1 | 8/2010 | DiLorenzo |
| 2010/0292602 A1 | 11/2010 | Worrell et al. |
| 2010/0302270 A1 | 12/2010 | Echauz et al. |
| 2011/0166430 A1 | 7/2011 | Harris et al. |
| 2011/0172554 A1 | 7/2011 | Leyde et al. |
| 2011/0201944 A1 | 8/2011 | Higgins et al. |
| 2011/0260855 A1 | 10/2011 | John et al. |
| 2011/0319785 A1 | 12/2011 | Snyder et al. |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 A1 | 11/1984 |
| EP | 0898460 | 3/1999 |
| EP | 1145735 A2 | 10/2001 |
| EP | 1145736 A2 | 10/2001 |
| EP | 1307260 | 5/2003 |
| EP | 1335668 | 8/2003 |
| EP | 1525551 | 4/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |

(56) References Cited

FOREIGN PATENT DOCUMENTS

| | | |
|---|---|---|
| WO | WO 2004/034881 A2 | 4/2004 |
| WO | WO 2004/034882 A2 | 4/2004 |
| WO | WO 2004/034883 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO 2006/020794 A2 | 2/2006 |
| WO | WO2006/035392 A1 | 4/2006 |

OTHER PUBLICATIONS

Spector et al.; High and Low Perceived Self-Control of Epileptic Seizures; Epilepsia, vol. 42(4), Apr. 2001; pp. 556-564.

Adjouadi, et al. A new mathematical approach based on orthogonal operators for the detection of interictal spikes in epileptogenic data. Biomed. Sci. Instrum. 2004; 40: 175-80.

Adjouadi, et al. Detection of interictal spikes and artifactual data through orthogonal transformations. J. Clin. Neurophysiol. 2005; 22(1):53-64.

Adjouadi, et al. Interictal spike detection using the Walsh transform. IEEE Trans. Biomed. Eng. 2004; 51(5): 868-72.

Aksenova, et al. Nonparametric on-line detection of changes in signal spectral characteristics for early prediction of epilepsy seizure onset. J. Automation and Information Sciences. 2004; 36(8): 35-45.

Aksenova, et al. On-line disharmony detection for early prediction of epilepsy seizure onset. 5th International Workshop Neural Coding 2003. Aulla (Italy) Sep. 20-25, 2003. (Abstract).

Andrzejak, et al. Bivariate surrogate techniques: necessity, strengths, and caveats. Physical Review E. 2003; 68: 066202-1-066202-15.

Andrzejak, et al. Testing the null hypothesis of the nonexistence of a preseizure state. Physical Review E. 2003; 67: 010901-1-010901-4.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. J Mol. Biol. 13: 238-252.

Baruchi, et al. Functional holography of complex networks activity—From cultures to the human brain. Complexity. 2005; 10(3): 38 R 51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Identification, and Control. 2003; 377-201: 313-317.

Bhattacharya, et al. Enhanced phase synchrony in the electroencephalograph gamma band for musicians while listening to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.

Chaovalitwongse, et al. EEG Classification in Epilepsy. Annals. 2004; 2 (37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versphase couplings. IEEE Trans. Biomed. Eng. 2003; 50(5):571-83.

Crichton, Michael, "Terminal Man", 1972, Ballantine Books, NY, NY, pp. 21-24, 32-33, 70-71, and 74-81.

D'Alessandro, et al. A multi-feature and multi-channel univariate selection process for seizure prediction. Clin. Neurophysiol. 2005; 116(3): 506-16.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

Drury, et al. Seizure prediction using scalp electroencephalogram. Exp. Neurol. 2003; 184 Suppl 1: S9-18.

Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.

Ebersole, J. S. In search of seizure prediction: a critique. Clin. Neurophysiol. 2005; 116(3): 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.

(56) References Cited

OTHER PUBLICATIONS

Faul, et al. An evaluation of automated neonatal seizure detection methods. Clin. Neurophysiol. 2005; 116(7): 1533-41.
Fein, et al. Common reference coherence data are confounded by power and phase effects. Electroencephalogr. Clin. Neurophysiol. 1988; 69:581-584.
Fell, et al. Linear inverse filtering improves spatial separation of nonlinear brain dynamics: a simulation study. J. Neurosci. Methods. 2000; 98(1): 49-56.
Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.
Fisher et al. 1999. Reassessment: Vagnerve stimulation for epilepsy, A report of the therapeutics and technology assessment subcommittee of the Academy of Neurology. Neurology.53: 666-669.
Franaszczuk et al.; An autoregressive method for the measurement of synchronization of interictal and ictal EEG signals; Biological Cybernetics, vol. 81; No. 1; pp. 3-9; 1999.
Gardner, A. B. A Novelty Detection Approach to Seizure Analysis from Intracranial EEG. Georgia Institute of Technology. Apr. 2004. A dissertation available at http://etd.gatech.edu/theses /available/ etd-04122004-132404/unrestricted/gardner _andrew_b_200405 _phd.pdf. Accessed Feb. 28, 2006.
Geva, et al. Forecasting generalized epileptic seizures from the EEG signal by wavelet analysis and dynamic unsupervised fuzzy clustering. IEEE Trans. Biomed. Eng. 1998; 45(10): 1205-16.
Gigola, et al. Prediction of epileptic seizures using accumulated energy in a multiresolution framework. J. Neurosci. Methods. 2004; 138(1-2): 107-111.
Guyon, I. An introduction to variable and feature selection. Journal of Machine Learning Research. 2003; 3:1157-1182.
Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.
Harrison, et al. Accumulated energy revised. Clin. Neurophysiol. 2005; 116(3):527-31.
Harrison, et al. Correlation dimension and integral do not predict epileptic seizures. Chaos. 2005; 15(3): 33106-1-15.
Hearst M. Trends & Controversies: Support Vector Machines. IEEE Intelligent Systems. 1998; 13: 18-28.
Hively, et al. Channel-consistent forewarning of epileptic events from scalp EEG. IEEE Trans. Biomed. Eng. 2003; 50(5): 584-93.
Hively, et al. Detecting dynamical changes in nonlinear time series. Physics Letters A. 1999; 258: 103-114.
Hively, et al. Epileptic Seizure Forewarning by Nonlinear Techniques. ORNL/TM-2000/333 Oak Ridge National Laboratory. Nov. 2000. Available at http://computing.ornl.gov/cse_home/staff/ hively/NBICradaAnnualRpt FY00.pdf. Accessed Feb. 28, 2006.
Hjorth, B. Source derivation simplifies topographical EEG interpretation. Am. J. EEG Technol. 1980; 20: 121-132.
Hsu, et al. A practical guide to support vector classification. Technical report, Department of Computer Science and Information Technology, National Taiwan University, 2003. Available at http:// www.csie.ntu.edu.tw/~cjlin/papers/guide/guide.pdf. Accessed Feb. 28, 2006.
Huynh, J. A. Evaluation of Gene Selection Using Support Vector Machine Recursive Feature Elimination. Arizona State University. May 26, 2004. (28 pages).
Huynh, J. A. Evaluation of Gene Selection Using Support Vector Machine Recursive Feature Elimination. Presentation slides. (41 pages) (May 26, 2004).
Iasemidis, et al. Adaptive epileptic seizure prediction system. IEEE Trans. Biomed. Eng. 2003; 50(5):616-27.
Iasemidis, et al. Automated Seizure Prediction Paradigm. Epilepsia. 1998; vol. 39, pp. 56.
Iasemidis, et al. Chaos Theory and Epilepsy. The Neuroscientist. 1996; 2:118-126.
Iasemidis, et al. Comment on "Inability of Lyapunov exponents to predict epileptic seizures." Physical Review Letters. 2005; 94(1):019801-1.
Iasemidis, et al. Detection of the Preictal Transition State in Scalp-Sphenoidal EEG Recordings. American Clinical Neurophysiology Society Annual Meeting, Sep. 1996. pp. C206.
Iasemidis, et al. Dynamical Interaction of the Epileptogenic Focwith Extrafocal Sites in Temporal Lobe Epilepsy (TLE). Ann. Neurol. 1997; 42, pp. 429. pp. M146.
Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.
Iasemidis, et al. Localizing Preictal Temporal Lobe Spike Foci Using Phase Space Analysis. Electroencephalography and Clinical Neurophysiology. 1990; 75, pp. S63-S64.
Iasemidis, et al. Long-term prospective on-line real-time seizure prediction. Clin. Neurophysiol. 2005; 116(3):532-44.
Iasemidis, et al. Long-Time-Scale Temporo-spatial Patterns of Entrainment of Preictal Electrocorticographic Data in Human Temporal Lobe Epilepsy. Epilepsia. 1990; 31(5):621.
Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.
Iasemidis, et al. Modelling of ECoG in temporal lobe epilepsy. Biomed. Sci. Instrum. 1988; 24: 187-93.
Iasemidis, et al. Nonlinear Dynamics of EcoG Data in Temporal Lobe Epilepsy. Electroencephalography and Clinical Neurophysiology. 1998; 5, pp. 339.
Iasemidis, et al. Phase space topography and the Lyapunov exponent of electrocorticograms in partial seizures. Brain Topogr. 1990; 2(3): 187-201.
Iasemidis, et al. Preictal Entrainment of a Critical Cortical Mass is a Necessary Condition for Seizure Occurrence. Epilepsia. 1996; 37, suppl. 5. pp. 90.
Iasemidis, et al. Preictal-Postictal Versus Postictal Analysis for Epileptogenic Focus Localization. J. Clin. Neurophysiol. 1997; 14, pp. 144.
Iasemidis, et al. Quadratic binary programming and dynamic system approach to determine the predictability of epileptic seizures. Journal of Combinatorial Optimization. 2001; 5: 9-26.
Iasemidis, et al. Quantification of Hidden Time Dependencies in the EEG within the Framework of Non-Linear Dynamics. World Scientific. 1993; pp. 30-47.
Iasemidis, et al. Spatiotemporal dynamics of human epileptic seizures. World Scientific. 1996; pp. 26-30.
Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. The Use of Dynamical Analysis of EEG Frequency Content in Seizure Prediction. American Electroencephalographic Society Annual Meeting, Oct. 1993.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18 (3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.

(56) References Cited

OTHER PUBLICATIONS

Le Van Quyen, et al. Anticipating epileptic seizures in real time by a non-linear analysis of similarity between EEG recordings. Neuroreport. 1999; 10(10):2149-55.

Le Van Quyen, et al. Author's second reply. The Lancet. 2003; 361:971.

Le Van Quyen, et al. Comparison of Hilbert transform and wavelet methods for the analysis of neuronal synchrony. J. Neurosci. Methods. 2001; 111(2):83-98.

Le Van Quyen, et al. Nonlinear analyses of interictal EEG map the brain interdependences in human focal epilepsy. Physica D. 1999; 127:250-266.

Le Van Quyen, et al. Preictal state identification by synchronization changes in long-term intracranial EEG recordings. Clin. Neurophysiol. 2005; 116(3):559-68.

Le Van Quyen, M. Anticipating epileptic seizures: from mathematics to clinical applications. C. R. Biol. 2005; 328(2):187-98.

Lehnertz, et al. Nonlinear EEG analysis in epilepsy: its possible use for interictal focus localization, seizure anticipation, and prevention. J. Clin. Neurophysiol. 2001; 18(3):209-22.

Lehnertz, et al. Seizure prediction by nonlinear EEG analysis. IEEE Eng. Med. Biol. Mag. 2003; 22(1):57-63.

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy—an overview. Int. J. Psychophysiol. 1999; 34(1):45-52.

Latka, et al. Wavelet analysis of epileptic spikes. Phys. Rev. E. 2003; 67 (5 Pt 1):052902 (6 pages).

Lemos, et al. The weighted average reference montage. Electroencephalogr. Clin. Neurophysiol. 1991; 79(5):361-70.

Li, et al. Fractal spectral analysis of pre-epileptic seizures in terms of criticality. J. Neural Eng. 2005; 2(2):11-16.

Li, et al. Linear and nonlinear measures and seizure anticipation in temporal lobe epilepsy. J. Comput. Neurosci. 2003; 15(3):335-45.

Li, et al. Non-linear, non-invasive method for seizure anticipation in focal epilepsy. Math. Biosci. 2003; 186(1):63-77.

Litt, et al. Prediction of epileptic seizures. Lancet Neurol. 2002; 1(1):22-30.

Litt, et al. Seizure prediction and the preseizure period. Curr. Opin. Neurol. 2002; 15(2):173-7.

Maiwald, et al. Comparison of three nonlinear seizure prediction methods by means of the seizure prediction characteristic. Physica D. 2004; 194:357-368.

Mangasarian, et al. Lagrangian Support Vector Machines. Journal of Machine Learning Research. 2001; 1:161-177.

Martinerie, et al. Epileptic seizures can be anticipated by non-linear analysis. Nat. Med. 1998; 4(10):1173-6.

McSharry, et al. Comparison of predictability of epileptic seizures by a linear and a nonlinear method. IEEE Trans. Biomed. Eng. 2003; 50(5):628-33.

McSharry, et al. Linear and non-linear methods for automatic seizure detection in scalp electro-encephalogram recordings. Med. Biol. Eng. Comput. 2002; 40(4):447-61.

McSharry, P. E. Detection of dynamical transitions in biomedical signals using nonlinear methods. Lecture Notes in Computer Science 2004; 3215:483-490.

Meng, et al. Gaussian mixture models of ECoG signal features for improved detection of epileptic seizures. Med. Eng. Phys. 2004; 26(5):379-93.

Mizuno-Matsumoto, et al. Wavelet-crosscorrelation analysis can help predict whether bursts of pulse stimulation will terminate after discharges. Clin. Neurophysiol. 2002; 113(1):33-42.

Mormann et al.; Seizure prediction: the long and winding road; Brain; vol. 130; No. 2; pp. 314-333; Sep. 28, 2006.

Mormann, et al. Automated detection of a preseizure state based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53(3):173-85.

Mormann, et al. Mean phase coherence as a measure for phase synchronization and its application to the EEG of epilepsy patients. Physica D. 2000; 144:358-369.

Mormann, et al. On the predictability of epileptic seizures. Clin. Neurophysiol. 2005; 116(3):569-87.

Mormann, et al. Seizure anticipation: from algorithms to clinical practice. Curr. Opin. Neurol. 2006; 19(2):187-93.

Navarro, et al. Seizure anticipation in human neocortical partial epilepsy. Brain. 2002; 125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57(2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.

Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18(3):223-45.

Rahimi, et al. On the Effectiveness of Aluminum Foil Helmets: An Empirical Study. Available at http://people.csail.mit.edu/rahimi/helmet/. Accessed Mar. 2, 2006.

Rothman et al.; Local Cooling: a therapy for intractable neocortical epilepsy; Epilepsy Currents; vol. 3; No. 5; pp. 153-156; Sep./Oct. 2003.

Robinson, et al. Steady States and Global Dynamics of Electrical Activity in the Cerebral Cortex. Phys. Rev. E. 1998; (58):3557-3571.

Rudrauf, et al. Frequency flows and the time-frequency dynamics of multivariate phase synchronization in brain signals. Neurolmage. 2005. (19 pages.).

Saab, et al. A system to detect the onset of epileptic seizures in scalp EEG. Clin. Neurophysiol, 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampin Limbic Epilepsy. Neurology. 1995; 45, Suppl. 4, pp. A 404.

Sackellares et al. Epileptic Seizures as Neural Resetting Mechanisms. Epilepsia. 1997; vol. 38, Sup. 3.

Sackellares et al. Measurement of Chaos to Localize Seizure Onset. Epilepsia. 1989; 30(5):663.

Sackellares et al. Relationship Between Hippocampal Atrophy and Dynamical Measures of EEG in Depth Electrode Recordings. American Electroencephalographic Society Annual Meeting, Sep. 1995. pp. A105.

(56) References Cited

OTHER PUBLICATIONS

Sackellares et al.; Predictability analysis for an automated seizure prediction algorithm; Journal of Clinical Neurophysiology; vol. 23; No. 6; pp. 509-520; Dec. 2006.
Sackellares, J. C. Epilepsy—when chaos fails. In: chaos in the brain? Eds. K. Lehnertz & C.E. Eiger. World Scientific. 2000 (22 pages).
Salant, et al. Prediction of epileptic seizures from two-channel EEG. Med. Biol. Eng. Comput. 1998; 36(5):549-56.
Schelter et al.; Testing statistical significance of multivariate time series analysis techniques for epileptic seizure prediction; Chaos; vol. 16; pp. 013108-1-10; Jan. 2006.
Schelter, et al. Testing for directed influences among neural signals using partial directed coherence. J. Neurosci. Methods. 2006; 152(1-2):210-9.
Schindler, et al. EEG analysis with simulated neuronal cell models helps to detect pre-seizure changes. Clin. Neurophysiol. 2002; 113(4):604-14.
Schwartzkroin, P. Origins of the Epileptic State. Epilepsia. 1997; 38, supply. 8, pp. 853-858.
Sheridan, T. Humans and Automation. NY: John Wiley. 2002.
Shoeb et al. Patient-specific seizure detection. MIT Computer Science and Artificial Intelligence Laboratory. 2004; pp. 193-194.
Snyder et al; The statistics of a practical seizure warning system; Journal of Neural Engineering; vol. 5; pp. 392-401; 2008.
Staba, et al. Quantitative analysis of high-frequency oscillations (80-500 Hz) recorded in human epileptic hippocampand entorhinal cortex. J. Neurophysiol. 2002; 88(4):1743-52.
Stefanski, et al. Using chaos synchronization to estimate the largest Lyapunov exponent of nonsmooth systems. Discrete Dynamics in Nature and Society. 2000; 4:207-215.
Subasi, et al. Classification of EEG signals using neural network and logistic regression. Computer Methods Programs Biomed. 2005; 78(2):87-99.
Szoka et al. Procedure for preparation of liposomes with large internal aqueospace and high capture volume by reverse phase evaporation. 1978. Proc. Natl Acad. Sci. USA. 75: 4194-4198.
Tass, et al. Detection of n: m Phase Locking from Noisy Data: Application to Magnetoencephalography. Physical Review Letters. 1998; 81(15):3291-3294.
Terry, et al. An improved algorithm for the detection of dynamical interdependence in bivariate time-series. Biol. Cybern. 2003; 88(2):129-36.
Tetzlaff, et al. Cellular neural networks (CNN) with linear weight functions for a prediction of epileptic seizures. Intl. J. of Neural Systems. 2003; 13(6):489-498.
Theiler, et al. Testing for non-linearity in time series: the method of surrogate data. Physica D. 1992; 58:77-94.
Tsakalis, K. S. Prediction and control of epileptic seizures: Coupled oscillator models. Arizona State University. (Slide: 53 pages) (No date).
Van Drongelen, et al. Seizure anticipation in pediatric epilepsy: use of Kolmogorov entropy. Pediatr. Neurol. 2003; 29(3): 207-13.
Van Putten, M. Nearest neighbor phase synchronization as a measure to detect seizure activity from scalp EEG recordings. J. Clin. Neurophysiol. 2003; 20(5):320-5.
Venugopal, et al. A new approach towards predictability of epileptic seizures: KLT dimension. Biomed Sci. Instrum. 2003; 39:123-8.
Vonck, et al. Long-term amygdalohippocampal stimulation for refractory temporal lobe epilepsy. Ann. Neurol. 2002; 52(5):556-65.
Vonck, et al. Long-term deep brain stimulation for refractory temporal lobe epilepsy. Epilepsia. 2005; 46(Suppl 5):98-9.
Vonck, et al. Neurostimulation for refractory epilepsy. Acta. Neurol. Belg. 2003; 103(4):213-7.
Weiss, P. Seizure prelude found by chaos calculation. Science News. 1998; 153(20):326.
Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.
Widman, et al. Reduced signal complexity of intracellular recordings: a precursor for epileptiform activity? Brain Res. 1999; 836(1-2):156-63.
Winterhalder, et al. Sensitivity and specificity of coherence and phase synchronization analysis. (In Press) Phys. Lett. A. 2006.
Winterhalder, et al. The seizure prediction characteristic: a general framework to assess and compare seizure prediction methods. Epilepsy Behav. 2003; 4(3):318-25.
Wong et al.; A stochastic framework for evaluating seizure prediction algorithms using hiden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 251-262; 2004.
Yang, et al. A supervised feature subset selection technique for multivariate time series. Available at http://infolab.usc.edu/DocsDemos/fsdm05.pdf. Accessed Mar. 2, 2006.
Yang, et al. CLe Ver: A feature subset selection technique for multivariate time series. T. B. Ho, D. Cheung, and H. Liu (Eds.): PAKDD. 2005; LNAI 3518: 516-522.
Yang, et al. Relation between Responsiveness to Neurotransmitters and Complexity of Epileptiform Activity in Rat Hippocampal CA1 Neurons. Epilepsia. 2002; 43(11):1330-1336.
Yatsenko, et al. Geometric Models, Fiber Bundles, and Biomedical Applications. Proceedings of Institute of Mathematics of NAS of Ukraine. 2004; 50 (Part 3):1518R1525.
Zaveri et al. Time-Frequency Analyses of Nonstationary Brain Signals. Electroencephalography and Clinical Neurophysiology. 1991; 79, pp. 28P-29P.
Zhang, et al. High-resolution EEG: cortical potential imaging of interictal spikes. Clin. Neurophysiol. 2003; 114(10):1963-73.
DiLorenzo, Daniel, U.S. Appl. No. 11/282,317 entitled "Closed-loop vagus nerve stimulation," filed Nov. 17, 2005.
Himes et al.; U.S. Appl. No. 12/716,132 entitled "Displaying and Manipulating Brain Function Data Including Enhanced Data Scrolling Functionality," filed Mar. 2, 2010.
Himes et al.; U.S. Appl. No. 12/716,147 entitled "Displaying and Manipulating Brain Function Data Including Filtering of Annotations," filed Mar. 2, 2010.
Higgins et al.; U.S. Appl. No. 13/026,961 entitled "Neurological monitoring and alerts," filed Feb. 14, 2011.
Chen et al.; Clinical utility of video-EEG monitoring; Perdiatric Neurology; vol. 12; No. 3; pp. 220-224; 1995.

\* cited by examiner

COMMUNICATION ERROR ALERTING IN AN EPILEPSY MONITORING SYSTEM

CROSS-REFERENCE TO RELATED APPLICATIONS

The present application is a continuation of pending U.S. patent application Ser. No. 12/020,507, filed Jan. 25, 2008, which claims benefit of U.S. Provisional Patent Application No. 60/897,551, filed Jan. 25, 2007, the disclosures of which are incorporated by reference herein in their entirety.

BACKGROUND OF THE INVENTION

The present invention relates generally to systems and methods for sampling and processing one or more physiological signals from a subject. More specifically, the present invention relates to monitoring of one or more neurological signals from a subject to determine a subject's susceptibility to a neurological event, communicating the subject's susceptibility to the subject, reducing a severity of seizures and/or preventing seizures. The invention also relates to continuously storing neurological signals from a subject to train algorithms to determine a subject's susceptibility for having a seizure.

Epilepsy is a neurological disorder of the brain characterized by chronic, recurring seizures. Seizures are a result of uncontrolled discharges of electrical activity in the brain. A seizure typically manifests itself as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of attention, loss of consciousness, and voiding of urine or stool.

A single seizure most often does not cause significant morbidity or mortality, but severe or recurring seizures (epilepsy) results in major medical, social, and economic consequences. Epilepsy is most often diagnosed in children and young adults, making the long-term medical and societal burden severe for this population of subjects. People with uncontrolled epilepsy are often significantly limited in their ability to work in many industries and usually cannot legally drive an automobile. An uncommon, but potentially lethal form of seizure is called status epilepticus, in which a seizure continues for more than 30 minutes. This continuous seizure activity may lead to permanent brain damage, and can be lethal if untreated.

While the exact cause of epilepsy is often uncertain, epilepsy can result from head trauma (such as from a car accident or a fall), infection (such as meningitis), stroke, or from neoplastic, vascular or developmental abnormalities of the brain. Approximately 70% of epileptic subjects, especially most forms that are resistant to treatment (i.e., refractory), are idiopathic or of unknown causes, and is generally presumed to be an inherited genetic disorder.

Demographic studies have estimated the prevalence of epilepsy at approximately 1% of the population, or approximately 2.5 million individuals in the United States alone. In order to assess possible causes and to guide treatment, epileptologists (both neurologists and neurosurgeons) typically evaluate subjects with seizures with brain wave electrical analysis and imaging studies, such as magnetic resonance imaging (MRI).

While there is no known cure for epilepsy, chronic usage of anticonvulsant and antiepileptic medications can control seizures in most people. For most cases of epilepsy, the disease is chronic and requires chronic medications for treatment. The anticonvulsant and antiepileptic medications do not actually correct the underlying conditions that cause seizures. Instead, the anticonvulsant and antiepileptic medications manage the subject's epilepsy by reducing the frequency of seizures. There are a variety of classes of anti-epileptic drugs (AEDs), each acting by a distinct mechanism or set of mechanisms.

AEDs generally suppress neural activity by a variety of mechanisms, including altering the activity of cell membrane ion channels and the susceptibility of action potentials or bursts of action potentials to be generated. These desired therapeutic effects are often accompanied by the undesired side effect of sedation, nausea, dizziness, etc. Some of the fast acting AEDs, such as benzodiazepine, are also primarily used as sedatives. Other medications have significant non-neurological side effects, such as gingival hyperplasia, a cosmetically undesirable overgrowth of the gums, and/or a thickening of the skull, as occurs with phenytoin. Furthermore, some AED are inappropriate for women of child bearing age due to the potential for causing severe birth defects.

An estimated 70% of subjects will respond favorably to their first AED monotherapy and no further medications will be required. However, for the remaining 30% of the subjects, their first AED will fail to fully control their seizures and they will be prescribed a second AED—often in addition to the first—even if the first AED does not stop or change a pattern or frequency of the subject's seizures. For those that fail the second AED, a third AED will be tried, and so on. Subjects who fail to gain control of their seizures through the use of AEDs are commonly referred to as "medically refractory." This creates a scenario in which 750,000 subjects or more in the United States have uncontrolled epilepsy. These medically refractory subjects account for 80% of the $12.5 billion in indirect and direct costs that are attributable to epilepsy in the United States.

A major challenge for physicians treating epileptic subjects is gaining a clear view of the effect of a medication or incremental medications. Presently, the standard metric for determining efficacy of the medication is for the subject or for the subject's caregiver to keep a diary of seizure activity. However, it is well recognized that such self-reporting is often of poor quality because subjects often do not realize when they have had a seizure, or fail to accurately record seizures.

If a subject is refractory to treatment with chronic usage of medications, surgical treatment options may be considered. If an identifiable seizure focus is found in an accessible region of the brain, which does not involve "eloquent cortex" or other critical regions of the brain, then resection is considered. If no focus is identifiable, or there are multiple foci, or the foci are in surgically inaccessible regions or involve eloquent cortex, then surgery is less likely to be successful or may not be indicated. Surgery is effective in more than half of the cases, in which it is indicated, but it is not without risk, and it is irreversible. Because of the inherent surgical risks and the potentially significant neurological sequelae from resective procedures, many subjects or their parents decline this therapeutic modality.

Some non-resective functional procedures, such as corpus callosotomy and subpial transection, sever white matter pathways without removing tissue. The objective of these surgical procedures is to interrupt pathways that mediate spread of seizure activity. These functional disconnection procedures can also be quite invasive and may be less effective than resection.

An alternative treatment for epilepsy that has demonstrated some utility is open loop Vagus Nerve Stimulation (VNS). This is a reversible procedure which introduces an electronic device which employs a pulse generator and an electrode to alter neural activity. The vagus nerve is a major nerve pathway that emanates from the brainstem and passes through the neck to control visceral function in the thorax and abdomen. VNS uses open looped, intermittent stimulation of the left vagus nerve in the neck in an attempt to reduce the frequency and intensity of seizures. See Fisher et al., "Reassessment: Vagus nerve stimulation for epilepsy, A report of the Therapeutics and Technology Assessment Subcommittee of the American Academy of Neurology," Neurology 1999; 53:666-669. While not highly effective, it has been estimated that VNS reduces seizures by an average of approximately 30-50% in about 30-50% of subjects who are implanted with the device. Unfortunately, a vast majority of the subjects who are outfitted with the Cyberonics® VNS device still suffer from un-forewarned seizures and many subjects obtain no benefit whatsoever.

Another recent alternative electrical stimulation therapy for the treatment of epilepsy is deep brain stimulation (DBS). Open-loop deep brain stimulation has been attempted at several anatomical target sites, including the anterior nucleus of the thalamus, the centromedian nucleus of the thalamus, and the hippocampus. The results have shown some potential to reduce seizure frequency, but the efficacy leaves much room for improvement.

Another type of electrical stimulation therapy for the treatment epilepsy has been proposed by NeuroPace, Inc., in which an implanted device is designed to detect abnormal electrical activity in the brain and respond by delivering electrical stimulation to the brain.

There have also been a number of proposals described in the patent literature regarding the use of predictive algorithms that purportedly can predict the onset of a seizure. When the predictive algorithm predicts the onset of a seizure, some type of warning is provided to the subject regarding the oncoming seizure or some sort of therapy is initiated. For example, see U.S. Pat. No. 3,863,625 to Viglione, U.S. Pat. No. 5,995,868 to Dorfmeister/Osorio, and U.S. Pat. No. 6,658,287 to Litt et al., the complete disclosures of which are incorporated herein by reference, describe a variety of proposed seizure prediction systems. However, to date, none of the proposed seizure prediction systems have shown statistically significant results.

While most seizures are short-lasting events that last only a few minutes, the seemingly random nature of the occurrence of seizures is what overshadows and destroys a subject's quality of life.

SUMMARY

Systems and methods for monitoring neurological signals in a patient are provided. The system includes: an implantable sensor adapted to collect neurological signals; an implantable assembly configured to sample the neurological signals collected by the sensor; and a rechargeable communication device external to the patient's body, said communication device configured to wirelessly communicate with the implantable assembly and to transmit a communication error alert to a caregiver advisory device in the event of a communication error between the implantable assembly and the communication device.

Also provided are methods and systems for sampling one or more physiological signals from the subject and processing such physiological signal(s) to monitor a subject's susceptibility or for a future neurological event. Such systems may also be adapted to provide an indication to the subject of their susceptibility for the neurological event, such as a warning or instruction, automatically initiate delivery of therapy to the subject, or allow or instruct the subject or a caregiver to administer a therapy prior to the onset of the seizure.

In preferred embodiments, the present invention is for managing epilepsy. Managing epilepsy includes the prevention or reduction of the occurrence of epileptic seizures and/or mitigating their effects, as well as alerting a subject when their susceptibility for having a seizure has been determined to be low. The method of preventing an epileptic seizure comprises characterizing a subject's susceptibility or susceptibility for a future seizure, and upon the determination that the subject has an elevated susceptibility for the seizure, communicating to the subject and/or a health care provider a warning or a therapy recommendation and/or initiating a therapy.

In one embodiment, the present invention provides ambulatory data collection systems and methods. The data collection systems of the present invention typically include one or more electrodes for sampling one or more physiological signals from the subject. In some embodiments, it may be desirable to include microelectrodes. In preferred embodiment, the physiological signals include signals that are indicative of neural activity in at least one portion of the brain, such as intracranial EEG ("iEEG" or "ECoG"), EEG, or a combination thereof. The electrodes may be intracranial electrodes (e.g., epidural, subdural, depth electrodes), extracranial electrodes (e.g., spike or bone screw electrodes, subcutaneous electrodes, scalp electrodes, dense array (256 channels) electrodes, etc.), or a combination thereof. While it is preferred to monitor signals directly from the brain, it may also be desirable to monitor brain activity using sphlenoidal electrodes, foramen ovale electrodes, intravascular electrodes, peripheral nerve electrodes, cranial nerve electrodes, or the like. While the remaining disclosure focuses on intracranial electrodes, it should be appreciated that any type of electrodes may be used to sample signals from the subject.

The one or more electrodes are typically in communication with an implanted assembly. The one or more electrodes may communicate with the implanted assembly (or directly with the external assembly as described below) with a wireless link, a wired link, or both. The implanted assembly is typically configured to facilitate transmission of a data signal that is representative of the one or more sampled physiological signals. The implanted assembly may be in wireless communication with an external assembly using any type of known uni-directional or bi-directional wireless link. Transmission of data and/or control signals between implantable assembly and the external assembly is typically carried out through a radiofrequency link, but may also be carried out through telemetry, magnetic induction, electromagnetic link, Bluetooth® link, Zigbee link, sonic link, optical link, other types of conventional wireless links, or combinations thereof.

In one embodiment, the external assembly will typically be configured to establish a one-way or two-way communication link with the implanted assembly using conventional telemetry handshaking protocols. The external assembly may allow the subject (or the subject's physician) to adjust parameters of the sampling of the physiological signal—such as adjusting the sampling rate, the data transmission rate, error correction, sampled channels, signal conditioning parameters (gain, filtering bandwidth, etc.), the type of data that is stored, or the like. In some embodiments, the implanted assembly will transmit a data signal that includes raw or processed physiological signal (e.g., intracranial EEG, EEG, etc.), one or more features that are extracted from the one or more signals, a signal that is indicative of a communication that is provided to the subject (e.g., warning, therapy recommendation, etc.) or a combination thereof.

At least one of the implanted assembly and external assembly may have a memory sub-system for storing data that is representative of the one or more physiological signals that are sampled with the one or more electrodes. In preferred embodiments, the data is stored in the memory sub-system of the external assembly. The data stored in the memory sub-system of the external assembly may thereafter be transferred to a FLASH drive, hard drive, a local computer, or to a remote server or computer system through a network connection (e.g., local area network (LAN), wide area network (WAN), the Internet, or the like). Preferably, the data will be transmitted to the subject's physician or computer station that is running software that can analyze the subject's physiological signals.

In some embodiments, at least one of the implanted assembly and external assembly will include one or more algorithms for analyzing the sampled physiological signal in real time. Such algorithms may be used as a seizure advisory system that is configured to measure the subject's susceptibility for having a neurological symptom. The systems of the present invention will comprise similar elements as the data collection system described above to facilitate sampling of EEG signals (and/or other physiological signals) from the subject that are indicative of the subject's susceptibility to seizure. The EEG signals may be analyzed by one or more analysis algorithms to determine when a subject is in an ictal state, a pro-ictal state or a contra-ictal state. An "ictal state" is used herein to refer to a seizure. The term "pro-ictal" is used herein to refer to a neurological state or condition characterized by an increased likelihood or higher susceptibility of transitioning to an ictal state. The term "contra-ictal" is used herein to refer to a neurological state or condition characterized by a low likelihood or susceptibility of transitioning to an ictal state and/or a pro-ictal state within a predetermined period of time. A more complete description of pro-ictal, contra-ictal and ictal states are described in co-pending and commonly owned patent application Ser. No. 12/020,450, filed Jan. 25, 2008, to Snyder et al., entitled "Systems and Methods for Identifying a Contra-ictal Condition in a Subject," the complete disclosure of which is incorporated herein by reference.

In one embodiment, a subject's susceptibility for a seizure can be estimated or derived from a neural condition which can be characterized as a point along a single or multivariable state space continuum. The term "neural state" is used herein to generally refer to calculation results or indices that are reflective of the state of the subject's neural system, but does not necessarily constitute a complete or comprehensive accounting of the subject's total neurological condition. The estimation and characterization of "neural state" may be based on one or more subject dependent parameters from the brain, such as electrical signals from the brain, including but not limited to electroencephalogram signals "EEG" and electrocorticogram signals "ECoG" or intracranial EEG (referred to herein collectively as EEG"), brain temperature, blood flow in the brain, concentration of AEDs in the brain or blood, etc.), heart rate, respiratory rate, chemical concentrations, etc.

The algorithms may analyze the sampled EEG signals in the implanted assembly, in the external assembly, or a portion of the advisory algorithm may be in both the implanted assembly and the external assembly. If the seizure advisory algorithm determines that the subject has entered a pro-ictal condition, the external assembly may be used to provide a warning, instruction, or other output to the subject that informs them of their transitioning from an inter-ictal or normal condition to the pro-ictal condition. The output from the external assembly may be visual, audio, tactile (e.g., vibratory), or some combination thereof. Such outputs from the external assembly may allow the user to make themselves safe (e.g., stop cooking, pull to the side of the road when driving, lie down, etc.) prior to the onset of the actual seizure or allow the subject to take an acute dosage of an AED to prevent or mitigate the seizure. Most importantly, the subject's will no longer be surprised by the seizures and will have more control over their life.

Such algorithms may also be used to provide insight to the subject and the subject's physician regarding the subject's specific seizure triggers. For example, if the subject's susceptibility to a seizure increases (and a warning is given) every time the subject intakes alcohol or a specific food, is sleep deprived, or is subject to a certain stimulus, the subject may be able to learn which triggers to avoid. Consequently, such seizure advisory systems will be able to provide quantifiable data to the subject and their physician regarding the subject-specific seizure triggers.

The seizure detection algorithm(s) may be used to detect the electrographic seizure onset and provide a seizure warning to the subject (or a care giver) just prior to the clinical manifestation of the seizure. Such a warning may or may not be sufficient to allow the subject to stop the seizure from occurring, but at a minimum, the warning will provide the subject or caregiver many seconds (or minutes) prior to the onset of the clinical seizure and allow the subject and/or caregiver to make the subject safe.

The systems described herein can also include an alert that is configured to indicate that there is a communication error between the implanted assembly and the external assembly. The alert can be disposed either in the internal assembly or in the external assembly. The alert can be a visible alert, an audible alert, a tactile alert, or any combination thereof.

The communication error can be a single type of communication error, or it can be a combination of different types of communication errors. For example, the communication error can be that the external assembly is out of communication range with the implanted assembly such that the external assembly is not receiving a data signal from the implanted device. The communication error can be that the external assembly is out of communication range with the implanted assembly for a predetermined amount of time. The communication error can be that the external assembly not receiving the data signal at an expected time or within an expected period of time. The external assembly can be configured to expect to receive a substantially continuous data signal, or the external assembly can be programmed to expect to receive a data signal periodically. The communication error can be that there is a gap in a data signal communication stream, such as missing packets of data in a numbered sequence of packets. The communication error can also be a data formatting error, such as an invalid cyclic redundancy. If the system detects a communication error an alert will be activated to indicate there is a communication error.

The systems that provide an alert when there is a communication error between the implanted assembly and the external assembly can also include an input on the external assembly that allows the subject to deactivate an alert function when the subject has a low likelihood of transitioning into the seizure condition, such as a contra-ictal condition. An alarm deactivation period can be less than a time period in which the subject is unlikely to transition into the seizure condition. In one example, the deactivation period is 45 minutes and the time period in which the subject is unlikely to transition into the seizure condition is 60 minutes. The deactivation period can be adjustable by the subject up to a maximum time period that does not exceed the time period in which the subject is unlikely to transition into the seizure condition.

Another aspect of the invention is a seizure advisory device. The seizure advisory device includes a user interface that comprises an indicator that indicates if the subject is at a low susceptibility to a seizure or a high susceptibility to a seizure. The seizure advisory device also includes an alert that is configured to provide an indication, such as an audible output, to the subject if the seizure advisory device is out of communication range with an implantable telemetry unit and is unable to accurately communicate the subject's susceptibility to the seizure.

One aspect of the invention is a method of activating an alert when there is a communication error between an implantable device and a device external to a subject. The method includes sampling a brain activity signal from a subject, transmitting a data signal indicative of the sampled brain activity signal from an implanted assembly to an external assembly outside of the subject, and activating an alert when there is a communication error between the implanted assembly and the external assembly. The method can include storing the data signal in the implanted assembly if there is a communication error, as well as attempting to retransmit the data signal after the error is detected.

One aspect of the invention is a method of informing a subject when a seizure advisory device is out of communication range with an implantable device. The method includes receiving a transcutaneously transmitted data signal indicative of the sampled brain activity signal from an implanted device and activating an alert when an expected data signal transmitted from the implanted device is not received by the seizure advisory device. The seizure advisory device can be configured to analyze the data signal to estimate the subject's susceptibility to a seizure. Alternatively, the implanted device is configured to analyze the data signal to estimate the subject's susceptibility to a seizure and the seizure advisory device is configured to communicate the estimated susceptibility to the subject. The data signal can be transmitted substantially continuously and comprises substantially real-time sampled brain activity signals.

The seizure advisory systems of the present invention may be used in conjunction with a therapy that may prevent the seizure from occurring, reduce the severity of the oncoming seizure, reduce the duration of the oncoming seizure, or the like. The therapy may be initiated in a closed loop within the system, or the therapy may be manually initiated by the subject or caregiver.

Depending on the level of the subject's susceptibility for a seizure, the output provided to the subject may take a variety of different forms. Some embodiments will provide an output to the subject that causes the subject to take an acute dosage of a pharmacological agent (e.g., neuro-suppressant, sedative such as a rapid onset benzodiazepine, AED or anticonvulsant, or other medication which exhibits seizure prevention effects). The advisory algorithm(s) may be used to characterize the subject's susceptibility for a future seizure. If the advisory algorithm determines that the subject is at an increased or elevated susceptibility for a future seizure, the system may provide an output to the subject and/or caregiver that facilitates the subject to take or the caregiver to provide an acute dosage of a pharmacological agent (such as an AED) to prevent the occurrence of the seizure or reduce the magnitude or duration of the seizure.

As used herein, the term "anti-epileptic drug" or "AED" generally encompasses pharmacological agents that reduce the frequency or susceptibility of a seizure. There are many drug classes that comprise the set of AEDs, and many different mechanisms of action are represented. For example, some medications are believed to increase the seizure threshold, thereby making the brain less likely to initiate a seizure. Other medications retard the spread of neural bursting activity and tend to prevent the propagation or spread of seizure activity. Some AEDs, such as the benzodiazepines, act via the GABA receptor and globally suppress neural activity. However, other AEDs may act by modulating a neuronal calcium channel, a neuronal potassium channel, a neuronal NMDA channel, a neuronal AMPA channel, a neuronal metabotropic type channel, a neuronal sodium channel, and/or a neuronal kainite channel.

Unlike conventional anti-epileptic drug treatments, which provide for an "open loop" chronic regimen of pharmacological agents, the present invention is able to manage seizures acutely while substantially optimizing the intake of the pharmacological agent by having the subject to take a pharmacological agent only when it is determined that the subject has transitioned to a higher susceptibility to a seizure, e.g., to a pro-ictal condition. Furthermore, with this new paradigm of seizure prevention, the present invention provides a new indication for pharmacotherapy. This new indication is served by several existing medications, including AEDs, given at doses which are sub-therapeutic to their previously known indications, such as acute AED administration for seizure termination or status epilepticus. Since this new indication is served by a new and much lower dosing regimen and consequently a new therapeutic window, the present invention is able to provide a correspondingly new and substantially reduced side effect profile and may reduce or eliminate tolerance effects of the AED. For example, the present invention allows the use of dosages that are lower than FDA-approved dosages for the various anti-epileptic agents. This dosing may be about 5% to about 95% lower than the FDA-recommended dose for the drug, and preferably at or below 90% of the FDA-recommended dose, and most preferably below about 50% of the FDA-recommended dose. But as can be appreciated, if the measured signals indicate a high susceptibility for a seizure, the methods and systems of the present invention may recommend taking an FDA or a higher than FDA approved dose of the AED to prevent the seizure. Such a paradigm has valuable application for subjects in which side effects of AEDs are problematic, particular sedation in general and teratogenicity in pregnant women or risk of teratogenicity in all women of child bearing age. A more complete description of using acute dosages of AEDs with a seizure advisory system is described in commonly owned U.S. patent application Ser. Nos. 11/321,897, 11/321,898, and 11/322,150 (all filed Dec. 28, 2005), the complete disclosures of which are incorporated herein by reference.

In another embodiment, the present invention provides a system that comprises an advisory algorithm that may be used to modify or alter the scheduling and/or dosing of a chronically prescribed pharmacological agent, such as an AED, to optimize or custom tailor the dosing to a particular subject at a particular point in time. This allows for (1) improved efficacy for individual subjects, since there is variation of therapeutic needs among subjects, and (2) improved response to variation in therapeutic needs for a given subject with time, resulting form normal physiological variations as well as from external and environmental influences, such as stress, sleep deprivation, the presence of flashing lights, alcohol intake and withdrawal, menstrual cycle, and the like The advisory algorithm may be used to characterize the subject's susceptibility for the future seizure. If the advisory algorithm determines that the subject is at an elevated susceptibility for an epileptic seizure or otherwise predicts the onset of a seizure, the system may provide an output that indicates or otherwise recommends or instructs the subject to take an accelerated or increased dosage of a chronically prescribed pharmacological agent. Consequently, the present invention may be able to provide a lower chronic plasma level of the AED and modulate the intake of the prescribed agent in order to decrease side effects and maximize benefit of the AED.

The seizure advisory systems of the present invention may be used by medically refractory subjects as well as by subjects who are chronically administering one or more AEDs. Advantageously, such a system may be used to titrate the chronic medications to a level that reduces the side effects, while still providing seizure prevention effects. If the seizure advisory systems of the present invention are able to determine that the subject has a high susceptibility with time periods that are longer than the time for the AED to reach a threshold plasma level and prevent the onset of the seizure, the subject may be able to take supplementary dosage of medication that is administered in response to the assessment of the higher susceptibility to the seizure. Such a method would reduce the subject's overall chronic intake of AEDs, while still preventing seizures in the subject.

The supplementary dosages may be the subject's standard dosage, a larger than standard dosage, or a smaller than standard dosage. The supplementary dosage could be the same AED that the subject takes chronically, or it could be a different AED. It may be desirable to have the dosage and/or type of medication be variable based on the ability of the algorithms to assess the particular subject's neurological condition. While the above description focuses on subject-administered AEDs, the systems of the present invention also encompass the use of implanted drug pumps that be automatically initiated by a control signal from the implanted assembly and/or the external assembly. Such implanted drug pumps may use similar dosing schemes as described above.

In other embodiments, the present invention provides seizure advisory systems in conjunction with automated or manual actuation of electrical neuromodulation. The electrical neuromodulation may be delivered to a peripheral nerve (e.g., vagus nerve stimulation ("VNS")), a cranial nerve (e.g., trigeminal nerve stimulation ("TNS")), directly to the brain tissue (e.g., deep brain stimulation (DBS), cortical stimulation, etc.), or any combination thereof.

In one configuration, the seizure advisory systems of the present invention may be used in conjunction with an existing implanted Cyberonics® VNS system. If the seizure advisory system of the present invention determines that the subject has transitioned to a pro-ictal condition, the system may provide an output to the subject so as to inform the subject to activate the VNS device with a wand. In alternative embodiments, the implanted assembly may include an integrated pulse generator that is configured to generate the neuromodulation signal that is delivered to a vagus nerve electrode.

Advantageously, the systems and methods of the present invention may be used to reduce subject anxiety and restore a sense of control in the subject's life, stop or reduce the duration or severity of the seizures, reduce or eliminate physical injuries to the subject, potentially increase vocational opportunities by allowing epileptic subjects to hold down jobs they wouldn't otherwise be able to have, resume their driving privileges, increase comfort with social interaction, and enable certain key activities of daily living.

For a further understanding of the nature and advantages of the present invention, reference should be made to the following description taken in conjunction with the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
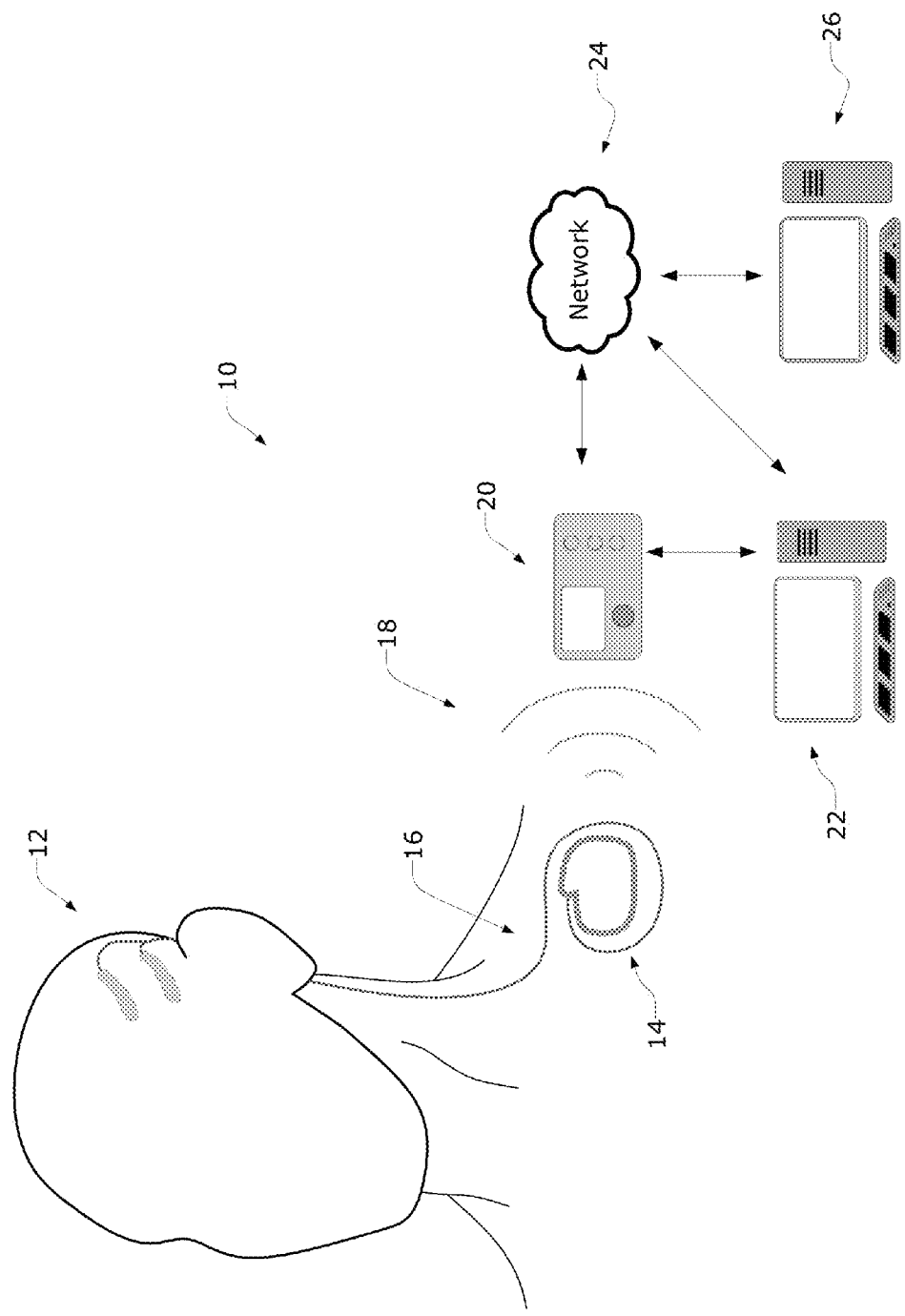
FIG. 1 illustrates one embodiment of a monitoring or data collection system which comprises one or more intracranial electrodes in communication with an external assembly through an implanted assembly.

Certain specific details are set forth in the following description and figures to provide an understanding of various embodiments of the invention. Certain well-known details, associated electronics and devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

The term "condition" is used herein to generally refer to the subject's underlying disease or disorder—such as epilepsy, depression, Parkinson's disease, headache disorder, etc. The term "state" is used herein to generally refer to calculation results or indices that are reflective a categorical approximation of a point (or group of points) along a single or multi-variable state space continuum of the subject's condition. The estimation of the subject's state does not necessarily constitute a complete or comprehensive accounting of the subject's total situation. As used in the context of the present invention, state typically refers to the subject's state within their neurological condition. For example, for a subject suffering from an epilepsy condition, at any point in time the subject may be in a different states along the continuum, such as an ictal state (a state in which a neurological event, such as a seizure, is occurring), a pro-ictal state (a state in which the subject has an increased risk of transitioning to the ictal state), an inter-ictal state (a state in between ictal states), a contra-ictal state (a state in which the subject has a low risk of transitioning to the ictal state within a calculated or predetermined time period), or the like. A pro-ictal state may transition to either an ictal or inter-ictal state.

The estimation and characterization of "state" may be based on one or more subject dependent parameters from a portion of the subject's body, such as electrical signals from the brain, including but not limited to electroencephalogram signals and electrocorticogram signals "ECoG" or intracranial EEG (referred to herein collectively as "EEG"), brain temperature, blood flow in the brain, concentration of AEDs in the brain or blood, changes thereof, etc. While parameters that are extracted from brain-based signals are preferred, the present invention may also extract parameters from other portions of the body, such as the heart rate, respiratory rate, blood pressure, chemical concentrations, etc.

An "event" is used herein to refer to a specific event in the subject's condition. Examples of such events include transition from one state to another state, e.g., an electrographic onset of seizure, end of seizure, or the like. For conditions other than epilepsy, the event could be an onset of a migraine headache, onset of a depressive episode, a tremor, or the like.

The occurrence of a seizure may be referred to as a number of different things. For example, when a seizure occurs, the subject is considered to have exited a "pro-ictal state" and has transitioned into the "ictal state". However, the electrographic onset of the seizure (one event) and/or the clinical onset of the seizure (another event) have also occurred during the transition of states.

A subject's "susceptibility" for a seizure is a measure of the likelihood of transitioning into the ictal state. The subject's susceptibility for seizure may be estimated by determining which "state" the subject is currently in. As noted above, the subject is deemed to have an increased susceptibility for transitioning into the ictal state (e.g., have a seizure) when the subject is determined to be in a pro-ictal state. Likewise, the subject may be deemed to have a low susceptibility for transitioning into the ictal state when it is determined that the subject is in a contra-ictal state.

While the discussion below focuses on measuring electrical signals generated by electrodes placed near, on, or within the brain or nervous system (EEG signals) of subjects and subject populations for the determination of a subject's susceptibility for having a seizure, it should be appreciated that the invention is not limited to measuring EEG signals or to determining the subject's susceptibility for having a seizure. For example, the invention could also be used in systems that measure one or more of a blood pressure, blood oxygenation indicator e.g. via pulse oximetry, temperature of the brain or of portions of the subject, blood flow measurements, ECG/EKG, heart rate signals, respiratory signals, chemical concentrations of neurotransmitters, chemical concentrations of medications, pH in the blood, or other physiological or biochemical parameters of a subject.

Furthermore, while the remaining discussion focuses on systems and method for measuring a subject's susceptibility for having a seizure, the present invention may also be applicable to monitoring other neurological or psychiatric disorders and determining the susceptibility for such disorders. For example, the present invention may also be applicable to monitoring and management of sleep apnea, Parkinson's disease, essential tremor, Alzheimer's disease, migraine headaches, depression, eating disorders, cardiac arrhythmias, bipolar spectrum disorders, or the like. The present invention may also be applicable to non-medical monitoring and management of events such as storms, earthquakes, social unrest, or other episodic events from which identification of a low susceptibility state may be useful. As can be appreciated, the features extracted from the signals and used by the algorithms will be specific to the underlying disorder that is being managed. While certain features may be relevant to epilepsy, such features may or may not be relevant to the state measurement for other disorders.

The devices and systems of the present invention can be used for long-term, ambulatory sampling and analysis of one or more physiological signals, such as a subject's brain activity (e.g., EEG). In many embodiments, the systems and methods of the present invention incorporate brain activity analysis algorithms that extract one or more features from the brain activity signals (and/or other physiological signals) and classifies, or otherwise processes, such features to determining the subject's susceptibility for having a seizure.

Some systems of the present invention may also be used to facilitate delivery of a therapy to the subject to prevent the onset of a seizure and/or abort or mitigate a seizure. Facilitating the delivery of the therapy may be carried out by outputting a warning or instructions to the subject or automatically initiating delivery of the therapy to the subject (e.g., pharmacological, electrical stimulation, focal cooling, etc.). The therapy may be delivered to the subject using an implanted assembly that is used to collect the ambulatory signals, or it may be delivered to the subject through a different implanted or external assembly.

A description of some systems that may be used to delivery a therapy to the subject are described in commonly owned U.S. Pat. Nos. 6,366,813 and 6,819,956, U.S. Patent Application Publication Nos. 2005/0021103 (published Jan. 27, 2005), 2005/0119703 (published Jun. 2, 2005), 2005/0021104 (published Jan. 27, 2005), 2005/0240242 (published Oct. 27, 2005), 2005/0222626 (published Oct. 6, 2005), and U.S. patent application Ser. No. 11/282,317 (filed Nov. 17, 2005), Ser. Nos. 11/321,897, 11/321,898, and 11/322,150 (all filed Dec. 28, 2005), the complete disclosures of which are incorporated herein by reference.

For subjects suspected or known to have epilepsy, the systems of the present invention may be used to collect data and quantify metrics for the subjects that heretofore have not been accurately measurable. For example, the data may be analyzed to (1) determine whether or not the subject has epilepsy, (2) determine the type of epilepsy, (3) determine the types of seizures, (4) localize or lateralize one or more seizure foci or seizure networks, (5) assess baseline seizure statistics and/or change from the baseline seizure statistics (e.g., seizure count, frequency, duration, seizure pattern, etc.), (6) monitor for sub-clinical seizures, assess a baseline frequency of occurrence, and/or change from the baseline occurrence, (7) measure the efficacy of AED treatments, deep brain or cortical stimulation, peripheral nerve stimulation, and/or cranial nerve stimulation, (8) assess the effect of adjustments of the parameters of the AED treatment, (9) determine the effects of adjustments of the type of AED, (10) determine the effect of, and the adjustment to parameters of, electrical stimulation (e.g., peripheral nerve stimulation, cranial nerve stimulation, deep brain stimulation (DBS), cortical stimulation, etc.), (11) determine the effect of, and the adjustment of parameters of focal cooling (e.g., use of cooling fluids, peltier devices, etc., to diminish or reduce seizures (see, for example, "Rothman et al., "Local Cooling: A Therapy for Intractable Neocortical Epilepsy," Epilepsy Currents, Vol. 3, No. 5, September/October 2003; pp. 153-156, (12) determine "triggers" for the subject's seizures, (13) assess outcomes from surgical procedures, (14) provide immediate biofeedback to the subject, (15) screen subjects for determining if they are an appropriate candidate for a seizure advisory system or other neurological monitoring or therapy system, or the like.

In a first aspect of the invention, the present invention encompasses a data collection system that is adapted to collect long term ambulatory brain activity data from the subject. In preferred embodiments, the data collection system is able to sample one or more channels of brain activity from the subject with one or more implanted electrodes. The electrodes are in wired or wireless communication with one or more implantable assemblies that are, in turn, in wired or wireless communication with an external assembly. The sampled brain activity data may be stored in a memory of the implanted assembly, external assembly and/or a remote location such as a physician's computer system. In alternative embodiments, it may be desirable to integrate the electrodes with the implanted assembly, and such an integrated implanted assembly may be in communication with the external assembly.

Unlike other conventional systems which have an implanted memory that is able to only store small epochs of brain activity before and after a seizure, the implantable assemblies of the present invention are configured to substantially continuously sample the physiological signals over a much longer time period (e.g., anywhere between one day to one week, one week to two weeks, two weeks to a month, or more) so as to be able to monitor fluctuations of the brain activity (or other physiological signal) over the entire time period. In alternative embodiments, however, the implantable assembly may only periodically sample the subject's physiological signals or selectively/aperiodically monitor the subject's physiological signals. Some examples of such alternative embodiments are described in commonly owned U.S. patent application Ser. Nos. 11/616,788 and 11/616,793, both filed Dec. 27, 2006, the complete disclosures of which are incorporated herein by reference.

When the memory is almost full, the system may provide the subject a warning so that the subject may manually initiate uploading of the collected brain activity data or the system may automatically initiate a periodic download of the collected brain activity data from a memory of the external assembly to a hard drive, flash-drive, local computer workstation, remote server or computer workstation, or other larger capacity memory system. In alternative embodiments, the external assembly may be configured to automatically stream the stored EEG data over a wireless link to a remote server or database. Such a wireless link may use existing WiFi networks, cellular networks, pager networks or other wireless network communication protocols. Advantageously, such embodiments would not require the subject to manually upload the data and could reduce the down time of the system and better ensure permanent capture of substantially all of the sampled data.

Another aspect of the invention is a system for monitoring a subject's susceptibility, or susceptibility, to a seizure. The system includes an electrode and an implanted communication assembly in communication with the electrode. The implanted communication assembly samples a neural signal with the electrode and substantially continuously transmits a data signal from the subject's body. The system also comprises an external assembly positioned outside the subject's body that is configured to receive and process the data signal to measure the subject's susceptibility to having a seizure. In alternative embodiments the implanted assembly processes the data and measures the subject's susceptibility of having a seizure, in which case only data indicative of the measured susceptibility is transmitted to the external assembly.

FIG. 1 illustrates an exemplary embodiment of a either a data collection system or monitoring system as described herein. System 10 includes one or more electrode arrays 12 that are configured to be implanted in the subject and configured to sample electrical activity from the subject's brain. The electrode array 12 may be positioned anywhere in, on, and/or around the subject's brain, but typically one or more of the electrodes are implanted within in the subject. For example, one of more of the electrodes may be implanted adjacent or above a previously identified epileptic network, epileptic focus or a portion of the brain where the focus is believed to be located. While not shown, it may be desirable to position one or more electrodes in a contralateral position relative to the focus or in other portions of the subject's body to monitor other physiological signals.

The electrode arrays 12 of the present invention may be intracranial electrodes (e.g., epidural, subdural, and/or depth electrodes), extracranial electrodes (e.g., spike or bone screw electrodes, subcutaneous electrodes, scalp electrodes, dense array electrodes), or a combination thereof. While it is preferred to monitor signals directly from the brain, it may also be desirable to monitor brain activity using sphlenoidal electrodes, foramen ovale electrodes, intravascular electrodes, peripheral nerve electrodes, cranial nerve electrodes, or the like. While the remaining disclosure focuses on intracranial electrodes for sampling intracranial EEG, it should be appreciated that the present invention encompasses any type of electrodes that may be used to sample any type of physiological signal from the subject.

In the configuration illustrated in FIG. 1, two electrode arrays 12 are positioned in an epidural or subdural space, but as noted above, any type of electrode placement may be used to monitor brain activity of the subject. For example, in a minimally invasive embodiment, the electrode array 12 may be implanted between the skull and any of the layers of the scalp. Specifically, the electrodes 12 may be positioned between the skin and the connective tissue, between the connective tissue and the epicranial aponeurosis/galea aponeurotica, between the epicranial aponeurosis/galea aponeurotica and the loose aerolar tissue, between the loose aerolar tissue and the pericranium, and/or between the pericranium and the calvarium. To improve signal-to-noise ratio, such subcutaneous electrodes may be rounded to conform to the curvature of the outer surface of the cranium, and may further include a protuberance that is directed inwardly toward the cranium to improve sampling of the brain activity signals. Furthermore, if desired, the electrode may be partially or fully positioned in openings disposed in the skull. Additional details of exemplary wireless minimally invasive implantable devices and their methods of implantation can be found in U.S. application Ser. No. 11/766,742, filed Jun. 21, 2007, the disclosure of which is incorporated by reference herein in its entirety.

Figure 2:
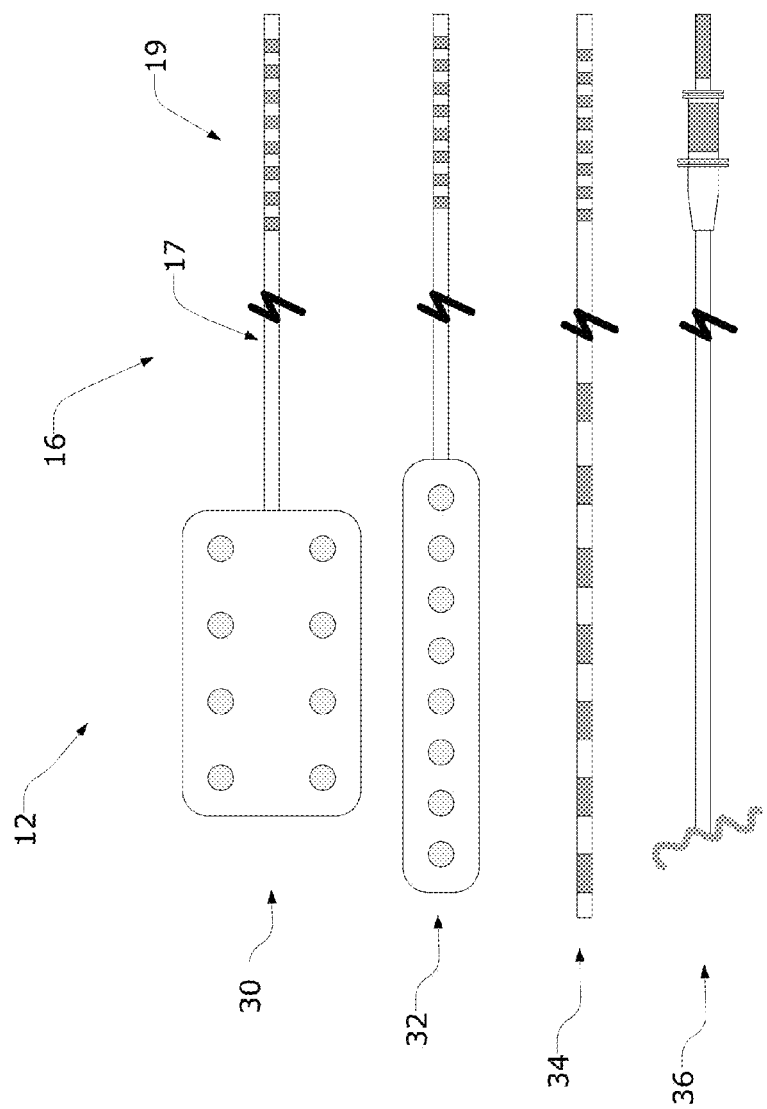
FIG. 2 illustrates examples of electrode arrays that may be used with the system of FIG. 1.

Some exemplary configurations of the electrode arrays 12 are shown in FIG. 2. Each of the illustrated electrode arrays has eight electrode contacts so as to provide sixteen 16 channels for monitoring the EEG signals. The electrode contacts may be bipolar or referential. It should be appreciated however, that while FIG. 2 illustrates sixteen 16 channels that are distributed over two electrode arrays, any number electrode arrays that have any number of contacts may be used with the present invention. In most embodiments, however, the system typically includes between about 1 and about 256 channels, and preferably between about 1 and about 32 channels, and more preferably between 8 and 32 channels that are distributed over 1 array and about 4 arrays. The array pattern and number of contacts on each array may be configured in any desirable pattern.

FIG. 2 specifically illustrates a 2×4 grid electrode array 30, a 1×8 strip electrode array 32, or a 1×8 depth electrode array 34. Each of the electrode arrays 12 will be coupled to the implanted assembly 14 with leads 16, unless they are wireless leads. The leads of each of the electrode arrays 12 will typically have a common lead body 17 and connector 19. The connector 19 may take any conventional or proprietary form, but in preferred embodiments is based on SCS/ICD technology. The electrode arrays could be used in either a bipolar or monopolar configuration.

If the system 10 includes the capability of providing stimulation of the peripheral nerve, such as the vagus nerve, the system may include a vagus nerve cuff 36, which includes a modified IS1 connector that is used for Cyberonics vagus nerve lead. The systems 10 of the present invention may also be configured to provide electrical stimulation to other portions of the nervous system (e.g., cortex, deep brain structures, cranial nerves, etc.). Stimulation parameters are typically about several volts in amplitude, 50 microsec to 1 milisec in pulse duration, and at a frequency between about 2 Hz and about 1000 Hz.

As shown in FIG. 1, the electrode arrays 12 are in wired communication with an implanted assembly 14 via the wire leads 16. The individual leads from the contacts (not shown) are placed in lead 16 and the lead 16 is tunneled between the cranium and the scalp and subcutaneously through the neck to the implanted assembly 14. Typically, implanted assembly 14 is implanted in a sub-clavicular pocket in the subject, but the implanted assembly 14 may be disposed somewhere else in the subject's body. For example, the implanted assembly 14 may be implanted in the abdomen or underneath, above, or within an opening in the subject's cranium (not shown).

Figure 3:
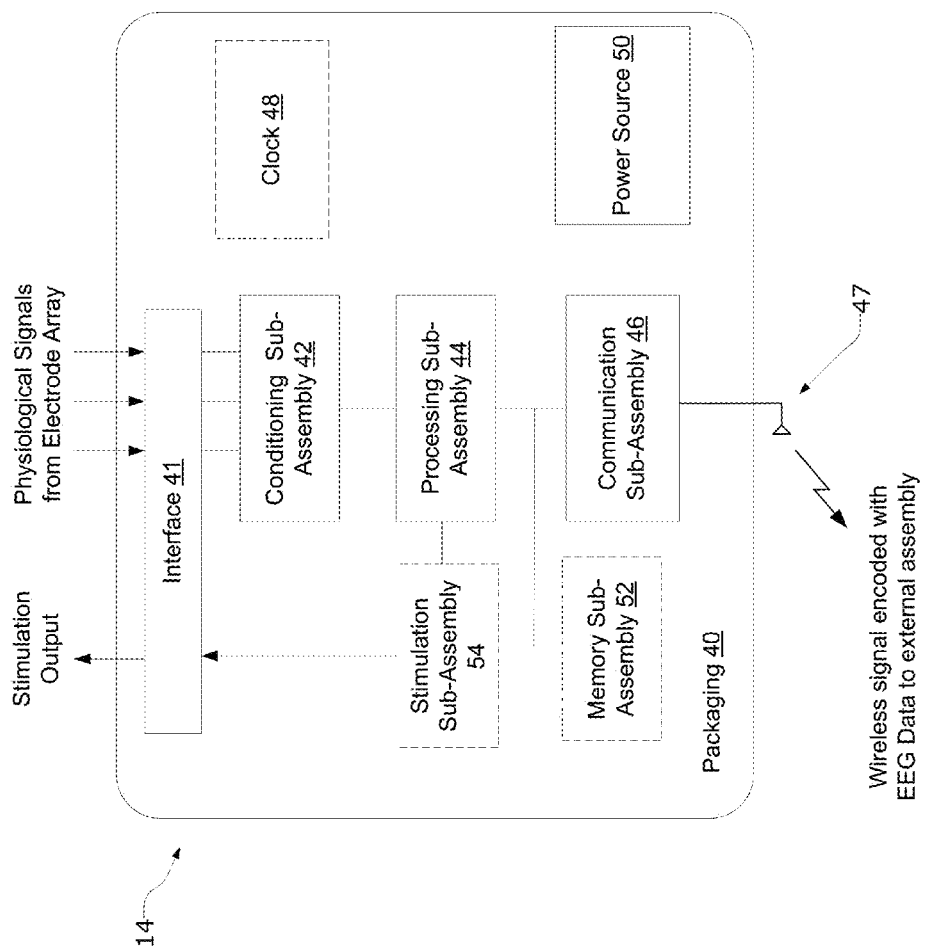
FIG. 3 is a simplified illustration of an implanted assembly that may be used with the system of FIG. 1.

Implanted assembly 14 can be used to pre-process EEG signals sampled by the electrode array 12 and transmit a data signal that is encoded with the sampled EEG data over a wireless link 18 to an external assembly 20, where the EEG data is permanently or temporarily stored. FIG. 3 illustrates a simplified embodiment of an exemplary implanted assembly 14. Implanted assembly 14 may comprise a cast epoxy packaging 40 that hermetically encapsulates the sub-assemblies of the implanted assembly 14. In other embodiments, the packaging 40 may include (i) biocompatible metals such as platinum, niobium, titanium, tantalum, and various alloys of these metals, (ii) biocompatible ceramics such as Aluminum Oxide ($Al_2O_3$), Zirconium Oxide ($ZO_2$), and Boron Nitride (BN), (iii) and any combination of ceramic, metal, and epoxy. Some examples of such embodiments are described in commonly owned U.S. Patent Application No. 61/017,504, filed Dec. 28, 2007, the complete disclosure of which is incorporated herein by reference.

Packaging 40 is preferably as small as possible and may have a similar packaging footprint as a spinal cord stimulator. Thus, the packaging typically has a volume between about 10 cubic centimeters to about 70 cubic centimeters and preferably about 30 cubic centimeters, but may be larger or smaller, depending on what components are disposed therein. Packaging 40 comprises an interface 41 for the connectors 19 of leads 16. The interface 41 will have at least the same number of input channels as the number of contacts in the electrode array, and may have more input channels than active contacts. Interface 41 may also have one or more bipolar output channels for delivering electrical stimulation to a peripheral nerve, brain tissue, cranial nerves, or other portions of the subject's body. Further details of an exemplary housing structure for the implanted assembly can be found in U.S. Application No. 61/017,504, filed Dec. 28, 2007, the disclosure of which is incorporated by reference herein in its entirety.

The interconnections between the components of implanted assembly 14 and external assembly 20 may be may be wired, wireless, digital, analog, or any combination thereof, and such electronic components may be embodied as hardware, software, firmware, or any combination thereof. While FIG. 3 shows one preferred embodiment of the electronic components of implanted assembly 14, it should be appreciated that the functionality performed by each of the sub-assemblies shown in FIG. 3 may be embodied in multiple sub-assemblies and the functionality carried out by multiple sub-assemblies of FIG. 3 may be combined into a single sub-assembly. Furthermore, some embodiments of the implanted assembly 14 may have additional functionalities not illustrated, while other embodiments may not have all of the functionality and/or electronic components that are illustrated in FIG. 3.

The electronic components of the implanted assembly will typically comprise a signal conditioning sub-assembly 42 that conditions the one or more EEG signals received from the interface 41. The signal conditioning sub-assembly 42 may perform amplification, combined to reduce common mode signal, filtering (e.g., lowpass, highpass, bandpass, and/or notch filtering), digital-to-analog conversion, or some combination thereof.

The electronic components of the implanted assembly 14 may optionally comprise dedicated circuitry and/or a microprocessor (referred to herein collectively as "processing sub-assembly 44") for further processing of the EEG signals prior to transmission to the external assembly 20. The further processing may include any combination of encryption, forward error correction, checksum or cyclic redundancy checks (CRC), or the like. The processing sub-assembly may comprise an ASIC, off the shelf components, or the like. In one embodiment processing sub-assembly 44 includes one or more multiple-core processors for processing data. Such multiple-core microprocessors provide faster processing, while consuming less power than multiple single core processors. Consequently, the life of the power source 44 may be prolonged. Some examples of suitable multiple-core processors include the Intel® Core 2 Duo Processor and the AMD® dual-core Opteron microprocessor.

Of course, while FIG. 3 illustrates a separate conditioning assembly 42 and processing sub-assembly, the two assemblies may be embodied in a single ASIC that performs the functionality of both assemblies 42, 44.

The implanted assembly 14 will also typically include both a clock 48 and a power source 50. The clock 48 is typically in the form of an oscillator and frequency synthesizer to provide synchronization and a time base for the signals transmitted from internal assembly and for signals received from external assembly 20. Power source 50 may be a non-rechargeable battery, a rechargeable battery, a capacitor, etc. One preferred power source is a medical grade rechargeable Li-Ion battery that is commonly used in other implantable devices. The rechargeable power source 50 may also be in communication with the communication sub-system 46 so as to receive power from outside the body by inductive coupling, radiofrequency (RF) coupling, etc. Such rechargeable power sources typically have a lifespan of between about 3 years and about 5 years. Power source 50 will generally be used to provide power to the other components of the implantable assembly 14.

In some embodiments, the implanted assembly 14 may optionally include a memory sub-system 52 (e.g., RAM) for permanently or temporarily storing or buffering the processed EEG signal. For example, memory sub-assembly 52 may be used as a buffer to temporarily store the processed EEG data if there are problems with transmitting the data to the external assembly. For example, if the external assembly's power supply is low, the memory in the external assembly is removed, or if the external assembly is out of communication range with the implantable assembly 14, the EEG data may be temporarily buffered in memory sub-assembly 52 and the buffered EEG data and the current sampled EEG data may be transmitted to the external assembly when the problem has been corrected. The buffer may be any size, but it will typically be large enough to store between about 1 megabyte and 100 megabytes of data. As can be appreciated, as technology improves and the capacity of memory cards improve, it is likely that many hundreds of gigabytes or hundreds of gigabytes of data may be buffered in the internal memory. Of course, in embodiments that do not have a memory sub-system 52 in the implanted assembly 14, any data that is sampled during the times in which the external assembly 20 is out of communication range with the implanted assembly 14, there may simply be gaps in the stored data.

In some embodiments the system 10 of the present invention may incorporate an alert that is activated to indicate that there is a communication error between the implanted assembly and the external assembly. Exemplary communication errors include, without limitation, when (1) the external assembly 20 is out of communication range with the internal assembly 14 such that the transmitted data signals are not received by the external assembly, (2) there is some other error in the transmission and receipt of data signals between the internal assembly 14 and external assembly, (3) self test error has been encountered, (4) memory card is full (or nearly full), or some combination thereof. Additional exemplary causes for an alert are discussed below in the more detailed discussion of the external assembly.

Typically, the alert is incorporated in the external assembly 20 so that the external assembly can provide a visual, audible, and/or tactile alert. Such an alert can indicate to the subject (or third party) that the external assembly 20 is not able to receive the RF signal from the implanted assembly 14 and/or that appropriate data transfer is not occurring. Moreover, the alert may reduce the likelihood of misplacing the external assembly 20, since in most embodiments, once the data transfer is interrupted, the alert may be activated by the system. In such a case, if the subject were to walk away from the external assembly 20 (e.g., leave the external assembly 20 on a table), the subject would not be advised of their susceptibility for seizure. If the subject did not realize that they did not have their external assembly 20 with them, the subject may assume that they are in a low susceptibility and perform activities on the assumption that their external assembly 20 would warn them of a changing to a state in which they were in a higher susceptibility to a seizure.

Additionally or alternatively, it may be possible to incorporate an alert in the implanted assembly 14 and the alert may provide a tactile warning (e.g., vibration) and/or audible alert to warn the subject that there is a data transmission error between the external assembly 20 and the implanted assembly 14.

In some embodiments the external assembly can be adapted so that it will expect to receive a data signal from the implanted assembly, and if it does not, the alert will be activated. The external assembly can be programmed to expect to receive a substantially continuous data signal from the implanted assembly, such that if the external assembly stops receiving a signal the alert will be activated. The external assembly can also be programmed to expect to receive a data signal periodically rather than substantially continuously. For example, the external assembly could expect to receive a signal every two seconds, and if it fails to receive a signal after a two second period of time, the alert will be activated. Thus, when the external assembly is adapted to expect a data signal periodically, the alert will be activated after a specified period of time passes without the external assembly receiving the data signal.

In some embodiments the communication error comprises a gap in the communication stream. For example, if the data signal comprises a numbered sequence of packets of information, and the external assembly receives a signal with missing packets of information within the sequence, the alert would be activated. The implanted assembly can be adapted to temporarily store the data signal so that if the external assembly detects a gap in the communication, the implanted assembly can attempt to retransmit the complete data signal data.

In some embodiments the communication error can include data formatting errors. An exemplary formatting error is an invalid cyclic redundancy check, but formatting errors as described herein include any other alteration of data during transmission or storage.

Figure 4:
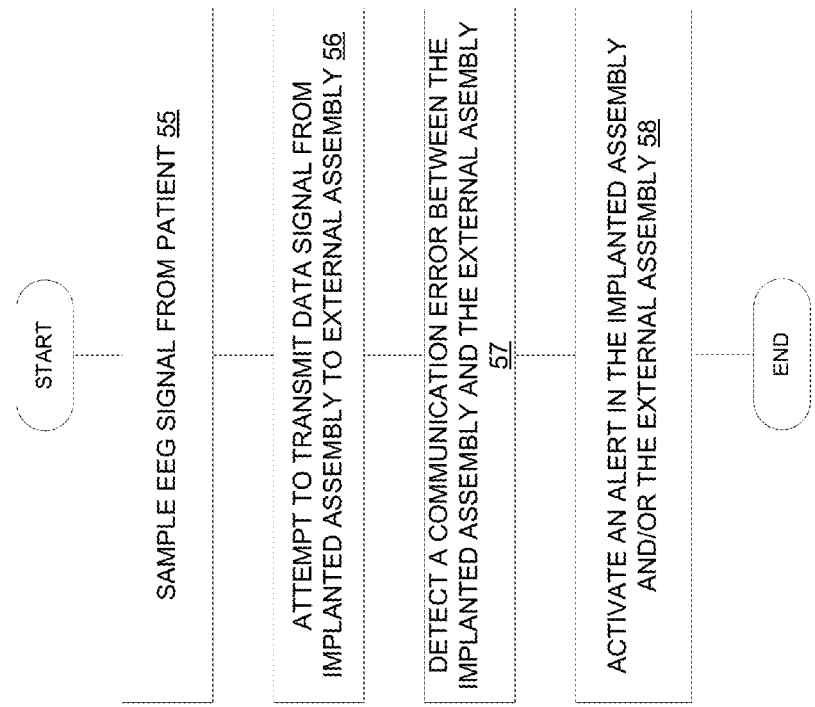
FIG. 4 is a simplified illustration of a method of alerting a subject of a communication error between the implanted assembly and external assembly.

FIG. 4 illustrates an exemplary method of activating an alert when there is an error transmitting a data signal between the implanted assembly and the external assembly. First, a brain signal, such as an EEG signal, is sampled from the subject at step 55. The implanted assembly then attempts to transmit a data signal which is indicative of the brain signal to the external assembly at step 56. If there is a communication error between the implanted assembly and the external assembly, step 57, the alert is activated, step 58, to notify the subject of the communication error. The implanted assembly can also attempt to retransmit the data signal between the implanted assembly and the external assembly if there is a communication error.

In some situations, the subject may be able to temporarily disable the alert and/or change the mode or parameters of the alert using a subject input. Such functionality may be carried out through providing a manual subject input—such as pressing a button on the external assembly 20.

Figure 6:
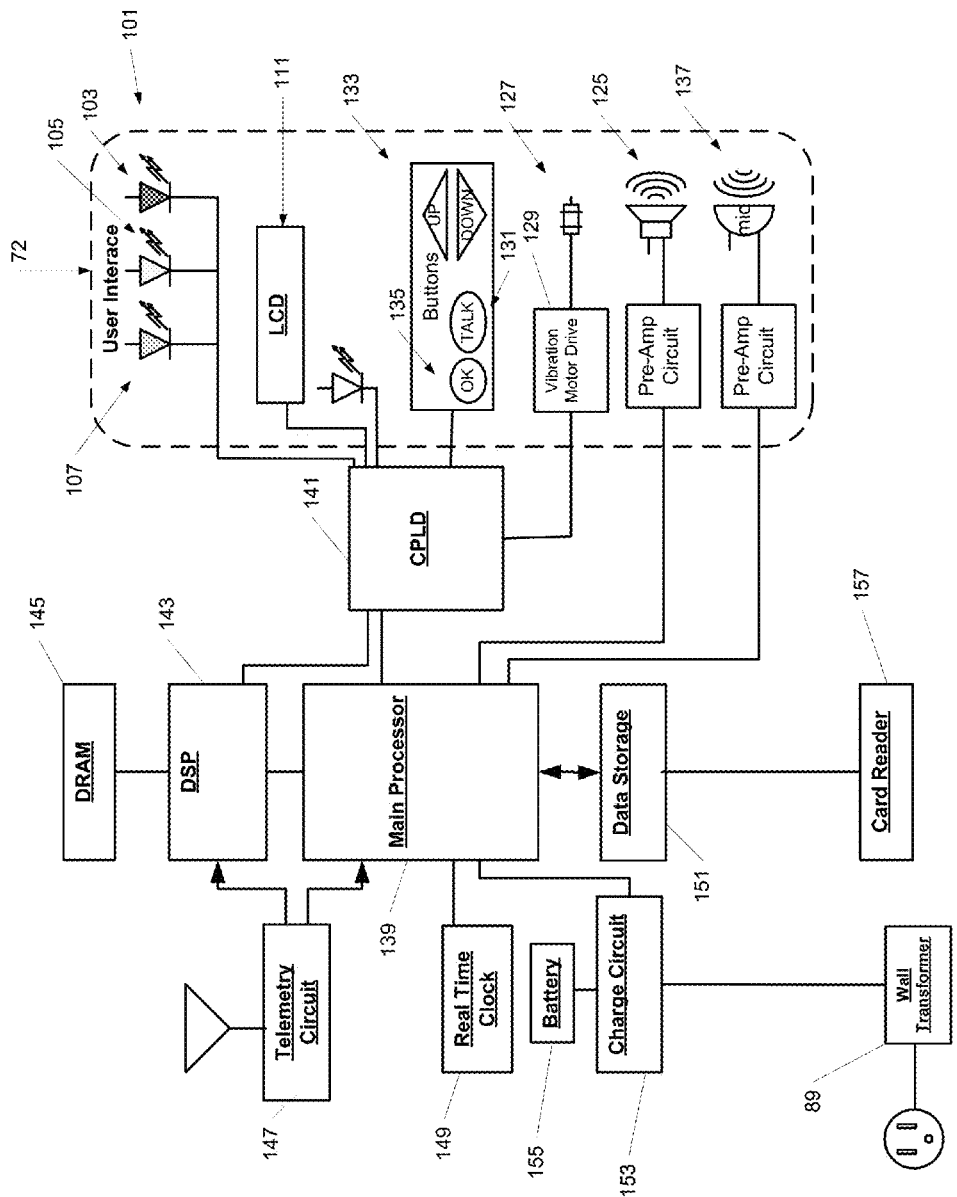
FIG. 6 is an alternative illustration of an external assembly that may be used with the system.

In some embodiments, external assembly 20 may be programmed to allow the subject to disable the alert if the subject is in one or more different neurological states. For example, if the subject is in a contra-ictal state in which the subject is at a low susceptibility to transitioning into an ictal state and/or a pro-ictal state in a period of time and did not want to carry the external assembly 20 with them (e.g., to take a shower and leave the external assembly 20 in the bedroom), the subject may disable the alert by using the buttons 131, 133, 135 or other user inputs on the external assembly 20 (FIG. 6). The disabling of the alert could last for a predetermined time period and then automatically be re-enabled, or the disabling of the alert may be continued until the subject manually re-enables the alert.

The subject and/or the physician may also customize the alert parameters to the subject. For example, some subjects may want to be immediately alerted if there is a communication error, while others may want a time delay before the alert is sounded.

Furthermore, if there is a prolonged alert (e.g., the subject leaves the house without the external assembly), the external assembly 20 may automatically disable the alert after a predetermined time and/or the alert may be manually disabled by a third party. To further reduce the likelihood of misplacing the external assembly 20 and ensuring that the subject is being monitored and advised, the external assembly 20 may comprise a communication assembly that facilitates the wireless communication with a remote party, such as the subject's caregiver, spouse, or friend (described in more detail below as the caregiver advisory device). Thus, if an alert is sounded that indicates a communication error, the communication assembly may send a wireless communication to the remote party to alert the third party that the subject is not being advised of their susceptibility to seizure. Typically, the wireless communication to the caregiver will be sent only after a predetermined time period has elapsed.

Tuning or reprogramming of the components of implanted assembly 14 may be carried out in vivo through communication sub-assembly 46. For example, the external assembly 20 and/or a dedicated programmer (controlled by physician) may be brought into communication range with the communication sub-assembly 46 and the reprogramming instructions may be uploaded into the processing sub-assembly.

Communication sub-assembly may include a magnetic reed switch (not shown) similar to those found in the Cyberonics® Vagus Nerve Stimulator or spinal cord stimulators. The magnetic reed switch would enable initiation of an electrode impedance check, self test, RAM check, ROM check, power supply checks, computer operating properly checks, electrode impedance check, or the like.

Implantable assembly 14 can be configured to substantially continuously sample the brain activity of the groups of neurons in the immediate vicinity of each of the contacts in the electrode array 12. The communication range between the implanted assembly 14 and the external assembly 20 is typically about 5 meters, but could be as short as requiring that the external assembly 20 contact the skin of the subject and up to 10 meters, or more. Sampling of the brain activity is typically carried out at a sampling rate above about 200 Hz, and preferably between about 200 Hz and about 1000 Hz, and most preferably between about 400 Hz and about 512 Hz, but it could be higher or lower, depending on the specific condition being monitored, the subject, and other factors. Each sample of the subject's brain activity will typically contain between about 8 bits per sample and about 32 bits per sample, and preferably between about 12 bits and 16 bits per sample. The wireless communication link 18 may have an overall data transfer rate between approximately 5 Kbits/sec and approximately 500 Kbits/sec, and preferably about approximately 50 kbits/sec. As can be appreciated, the over air data transfer rate of the implanted assembly could be considerably higher (e.g., 2 Mbits/sec), which would allow for a lower transmit duty cycle which will result in power savings.

For example, if each communication transmission to the external assembly includes one EEG sample per transmission, and the sample rate is 400 Hz and there are 16 bits/sample, the data transfer rate from the implantable assembly 14 to the external assembly 20 is at least about 6.4 Kbits/second/channel. If there are 16 channels, the total data transfer rate for the wireless communication link 18 between the implanted assembly 14 and the external assembly 20 would be about 102 Kbits/second.

While substantially continuous sampling and transmission of brain activity is preferred, in alternative embodiments, it may be desirable to have the implantable assembly 14 sample the brain activity of the subject in a non-continuous basis or the sampling rate may vary over the period of monitoring. In such embodiments, the implantable assembly 14 may be configured to sample the brain activity signals periodically (e.g., a burst of sampling every 5 seconds) or aperiodically. For example, it may be desirable to reduce or increase the sampling rate when a subject has gone to sleep.

To enable the high data transfer rates of the present invention, the wireless communication link 18 provided by the communication sub-assembly 46 is typically in the form of an electromagnetic radiofrequency communication link. Conventional devices typically use a slower communication link (e.g., that is designed for low data transfer rates and long link access delays) and transmit data out on a non-continuous basis. In contrast, the present invention uses a fast access communication link that transmits smaller bursts of data (e.g., single or small number of EEG samples from each of the channels at a time) on a substantially continuous basis so as to allow for substantially real-time analysis of the EEG data. The radiofrequency used to transfer data between the implantable assembly 14 and external assembly 20 is at a frequency typically between 13.56 MHz and 10 GHz, preferably between about 900 MHz and about 2.4 GHz, more preferably at about 2.4 GHz, or between about 900 MHz and about 928 MHz. One potentially useful communication sub-assembly is a 900 MHz ISM telemetry transmitter. If it is desired to avoid FCC regulations, it may be desirable to use telemetry at low frequency, such as below 9 Khz.

As can be appreciated, while the aforementioned frequencies are the preferred frequencies, the present invention is not limited to such frequencies and other frequencies that are higher and lower may also be used. For example, it may be desirable us use the MICS (Medical Implant Communication Service band) that is between 402-405 MHz to facilitate the communication link.

In order to facilitate data transmission from the implanted assembly 14 to the external assembly 20, the antennas 47 and 62 of the implantable assembly 14 and external assembly 14, respectively, must be maintained in communication range of each other. The frequency used for the wireless communication link has a direct bearing on the communication range. Typically, the communication range is typically at least one foot, preferably between about one foot and about twenty feet, and more preferably between about six feet and sixteen feet. As can be appreciated, however, the present invention is not limited to such communication ranges, and larger or smaller communication ranges may be used. For example, if an inductive communication link is used, the communication range will be smaller than the aforementioned range; but if higher frequencies are used, the communication range may be larger than twenty feet.

While not illustrated in FIGS. 1 to 4, the systems 10 of the present invention may also make use of conventional or proprietary forward error correction ("FEC") methods to control errors and ensure the integrity of the data transmitted from the implantable assembly 14 to the external assembly 20. Such forward error correction methods may include such conventional implementations such as cyclic redundancy check ("CRC"), checksums, or the like.

In some situations, instead of a wireless link between the implanted assembly 14 and the external assembly 20, it may be desirable to have a wire running from the subject-worn data collection assembly 20 to an interface (not shown) that could directly link up to the implanted assembly 14 that is positioned below the subject's skin. For example, the interface may take the form of a magnetically attached transducer, as with cochlear implants. This could enable higher rates of data transmission between the implanted assembly 14 and the external assembly 20.

Figure 5:
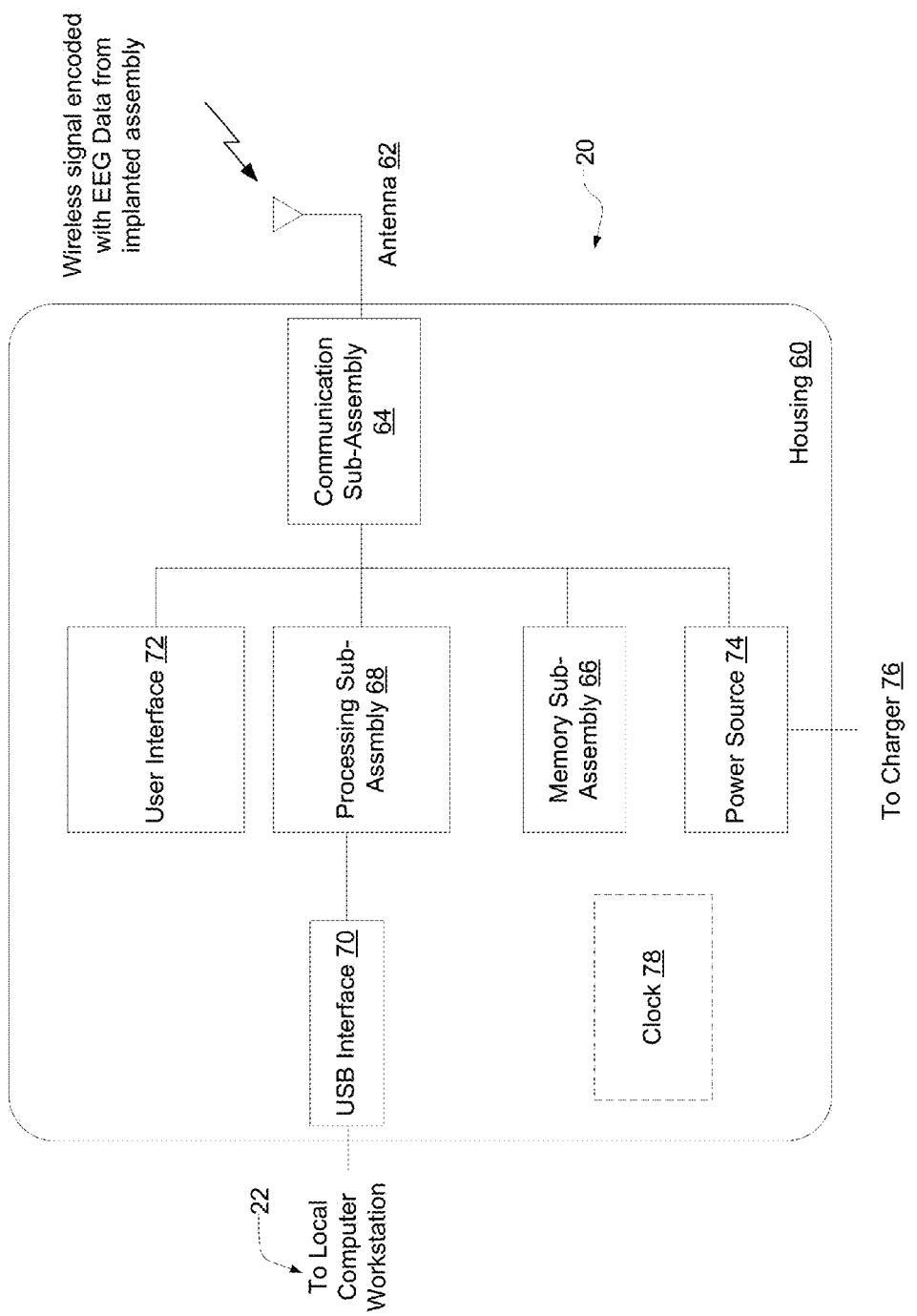
FIG. 5 is a simplified illustration of an external assembly that may be used with the system of FIG. 1.

FIG. 5 illustrates a simplified embodiment of external assembly 20. For example, in alternative embodiments the functionality performed by a single sub-assembly shown in FIG. 5 may be embodied in multiple sub-assemblies, and/or the functionality carried out by multiple sub-assemblies of FIG. 5 may be combined into a single sub-assembly. Furthermore, other embodiments of the external assembly 20 may have additional functionalities not illustrated, while other embodiments may not have all of the functionality and/or electronic components that are illustrated in FIG. 5. External assembly 20 is typically portable and comprises a housing 60 that is of a size that allows for storage in a purse or pocket of the subject. The handheld housing 60 typically has a form factor of a MP3 player (e.g., Apple iPod), cellular phone, personal digital assistant (PDA), pager, or the like. In some embodiments, the components of the external assembly 20 may be integrated within a housing of such consumer electronics devices.

Figure 7:
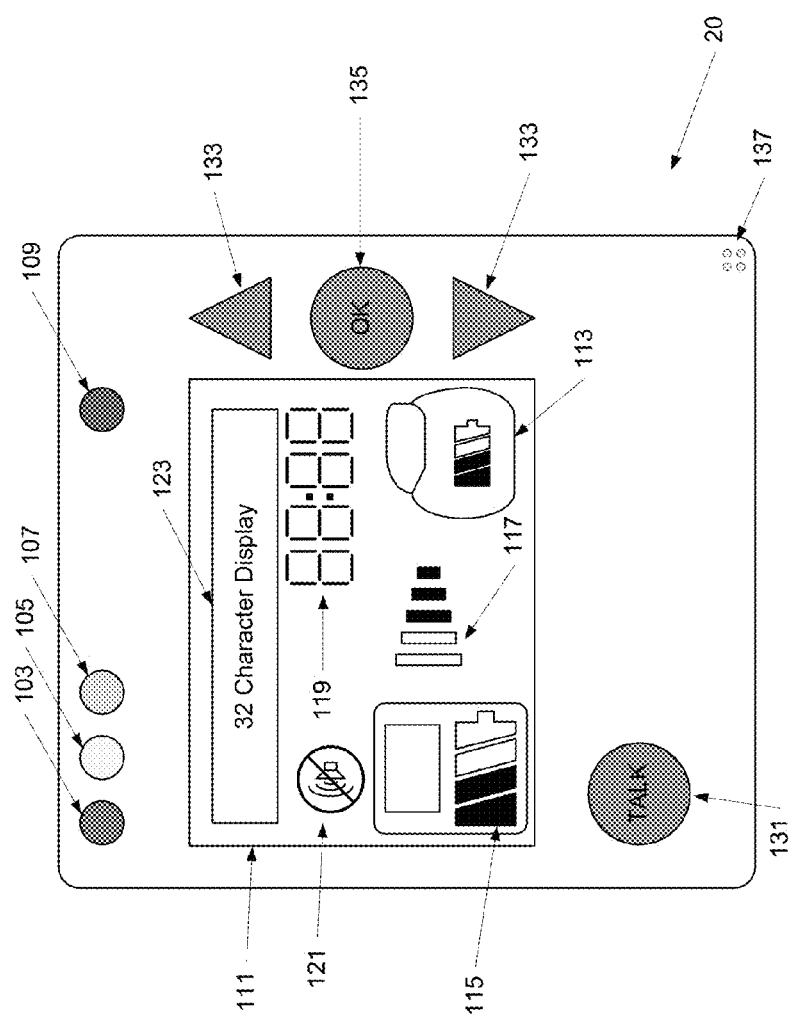
FIG. 7 illustrates an exemplary user interface including outputs of an exemplary external assembly that may be used with the system.
Figure 8:
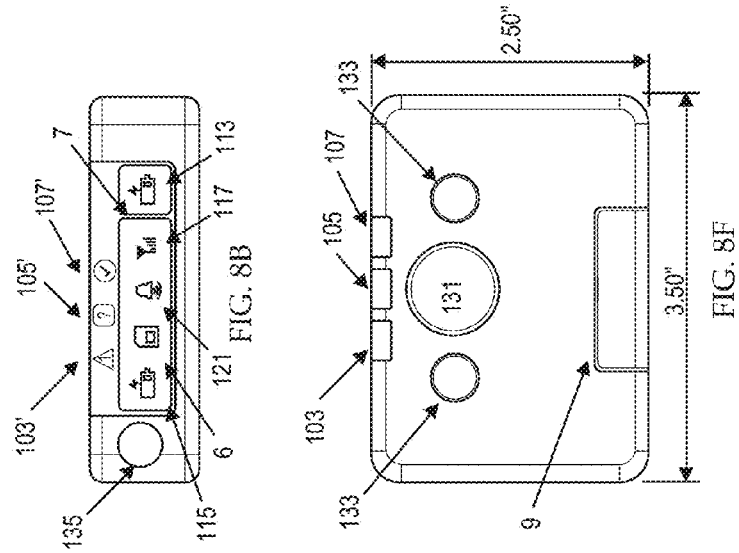
FIG. 8 illustrates an exemplary external assembly that may be used with the system.

FIGS. 6, 7, and 8 illustrate alternative embodiments of external assembly 20.

The illustrated external assembly shows a user interface 72 that includes a variety of indicators for providing system status and alerts to the subject. User interface 72 may include one or more indicators 101 that indicate the subject's brain state. In the illustrated embodiment, the output includes light indicators 101 (for example, LEDs) that comprise one or more (e.g., preferably two or more) discrete outputs that differentiate between a variety of different brain states. In the illustrated embodiment, the brain state indicators 101 include a red light 103, yellow/blue light 105, and a green light 107 for indicating the subject's different brain states (described more fully below). In some configurations the lights may be solid, blink or provide different sequences of flashing to indicate different brain states. If desired, the light indicators may also include an "alert" or "information" light 109 that is separate from the brain state indicators so as to minimize the potential confusion by the subject.

External assembly 20 may also include a liquid crystal display ("LCD") 111 or other display for providing system status outputs to the subject. The LCD 111 generally displays the system components' status and prompts for the subject. For example, as shown in FIG. 7, LCD 111 can display indicators, in the form of text or icons, such as, for example, implantable device battery strength 113, external assembly battery strength 115, and signal strength 117 between the implantable device and the external assembly 20. If desired, the LCD may also display the algorithm output (e.g., brain state indication) and the user interface 72 may not require the separate brain state indicator(s) 101. The output on the LCD is preferably continuous, but in some embodiments may appear only upon the occurrence of an event or change of the system status and/or the LCD may enter a sleep mode until the subject activates a user input. LCD 111 is also shown including a clock 119, audio status 121 (icon shows PAD is muted), and character display 123 for visual text alerts to the subject—such as an estimated time to seizure or an estimated "contra-ictal" time. While not shown in FIG. 7, the LCD 111 may also indicate the amount of free memory remaining on the memory card.

FIGS. $8_a$-$8_g$ illustrate a variety of different views of another embodiment of the external assembly. FIGS. $8_a$ and $8_b$ are two alternative top plan views of the external assembly. FIGS. $8_c$ and $8_e$ are opposing side views. FIG. $8_d$ is a back view. FIG. $8_f$ is a front view. FIG. $8_g$ is a bottom view. The illustrated embodiment of FIG. 8 is a pager-style external assembly that may be carried on a clip (not shown) that may be used to couple the external assembly to the subject's belt or bag. The typical dimensions of this embodiment of the external assembly are typically 1.00"×2.50"×3.50", but may be larger or smaller as desired.

Similar to the other embodiments, the external assembly of FIG. 8 comprises a plurality of user inputs 131, 133, 135, brain state indicators 101 and outputs that indicate a state of the system (e.g., LCD 111). As shown in FIG. $8_b$, the LCD may comprise a plurality of different icons on the LCD 111 to indicate the state of the system. For example, the illustrated embodiment includes an external assembly battery indicator 115, implanted device battery indicator 113, telemetry signal strength indicator 117, volume indicator 121, and a memory card status indicator 6. To differentiate between the implanted device system state and external assembly system state, it may be desirable to provide a physical separation 7 between the icons. The physical separation element 7 could be a physical barrier that overlays the LCD, two separate LCDs that are spaced from each other, or simply a discernable separation between icons on the LCD.

The LCD 111 and brain state indicators 101 are typically viewable by the subject when it is attached to the subject's belt. As such, the subject need only glance down onto the top surface of the PAD when an audible or tactile indication is provided that indicates a subject's brain state or change thereof.

In the embodiment of FIG. $8_a$, the brain state indicators 103, 105, 107 may be positioned along the junction of the top surface and front surface so as to be viewable from multiple angles. In another embodiment shown in FIG. $8_b$, either in addition to the brain state indicators 103, 105, 107 on the front surface (FIG. $8_f$) or as an alternative to the brain state indicator on the front surface, the top surface may have brain state indicators 103', 105', 107' that are viewable from the top surface. In the embodiment shown in $8_b$, the brain state indicators 103', 105', 107' on the top surface may be different colored and different shaped to further differentiate between the different brain states. In both embodiments of FIGS. $8_a$ and $8_b$, the acknowledgement input 135 may be positioned along a top surface of the external assembly so that the acknowledgement input 135 is readily accessible to the subject when the brain state indicator 101 is activated.

The front surface of the external assembly may also comprise a door 9 that houses the removable data card an on/off input button (not shown). When opened, the subject may replace the full (or defective) data card with a new card. Alternatively, if the subject desires to turn on or off the external assembly, the subject may activate the on/off input. Typically, the subject will keep the external assembly on at all times, but in instances which require the external assembly to be off (e.g., on an airplane), the subject may have the ability to turn off the external assembly and stop the transmission of the data signal from the implanted device— which may help to conserve battery power of the external assembly and implanted device.

Referring again to FIG. 6, external assembly 20 may also include a speaker 125 and a pre-amp circuit to provide audio outputs to the subject (e.g., beeps, tones, music, recorded voice alerts, etc.) that may indicate brain state or system status to the subject. User interface 72 may also include a vibratory output device 127 and a vibration motor drive 129 to provide a tactile alert to the subject, which may be used separately from or in conjunction with the visual and audio outputs provided to the subject. The vibratory output device 127 is generally disposed within external assembly 20, and is described in more detail below. Depending on the desired configuration any of the aforementioned outputs may be combined to provide information to the subject.

The external assembly 20 preferably comprises one or more subject inputs that allow the subject to provide inputs to the external assembly. In the illustrated embodiment, the inputs comprise one or more physical inputs (e.g., buttons 131, 133, 135) and an audio input (in the form of a microphone 137 and a pre-amp circuit).

Similar to conventional cellular phones, the inputs 131, 133, 135 may be used to toggle between the different types of outputs provided by the external assembly. For example, the subject can use buttons 133 to choose to be notified by tactile alerts such as vibration rather than audio alerts (if, for example, a subject is in a movie theater). Or the subject may wish to turn the alerts off altogether (if, for example, the subject is going to sleep). In addition to choosing the type of alert, the subject can choose the characteristics of the type of alert. For example, the subject can set the audio tone alerts to a low volume, medium volume, or to a high volume.

Some embodiments of the external assembly 20 will allow for recording audio, such as voice data. A dedicated voice recording user input 131 may be activated to allow for voice recording. In preferred embodiments, the voice recording may be used as an audio subject seizure diary. Such a diary may be used by the subject to record when a seizure has occurred, when an aura or prodrome has occurred, when a medication has been taken, to record subject's sleep state, stress level, etc. Such voice recordings may be time stamped and stored in data storage of the external assembly and may be transferred along with recorded EEG signals to the physician's computer. Such voice recordings may thereafter be overlaid over the EEG signals and used to interpret the subject's EEG signals and improve the training of the subject's customized algorithm, if desired.

The one or more inputs may also be used to acknowledge system status alerts and/or brain state alerts. For example, if the external assembly provides an output that indicates a change in brain state, one or more of the LEDs 101 may blink, the vibratory output may be produced, and/or an audio alert may be generated. In order to turn off the audio alert, turn off the vibratory alert and/or to stop the LEDs from blinking, the subject may be required to acknowledge receiving the alert by actuating one of the user inputs (e.g., button 135).

While the external assembly is shown having inputs 131, 133, 135, any number of inputs may be provided on the external assembly. For example, in one alternate embodiment, the external assembly may comprise only two input buttons. The first input button may be a universal button that may be used to scroll through output mode options. A second input button may be dedicated to voice recording. When an alert is generated by the external assembly, either of the two buttons may be used to acknowledge and deactivate the alert. In other embodiments, however, there may be a dedicated user input for acknowledging the alerts.

External assembly 20 may comprise a main processor 139 and a complex programmable logic device (CPLD) 141 that control much of the functionality of the external assembly. In the illustrated configuration, the main processor and/or CPLD 141 control the outputs displayed on the LCD 111, generates the control signals delivered to the vibration device 127 and speaker 125, and receives and processes the signals from buttons 131, 133, 135, microphone 137, and a real-time clock 149. The real-time clock 149 may generate the timing signals that are used with the various components of the system.

The main processor may also manage a data storage device 151, provides redundancy for a digital signal processor 143 ("DSP"), and manage the telemetry circuit 147 and a charge circuit 153 for a power source, such as a battery 155.

While main processor 139 is illustrated as a single processor, the main processor may comprise a plurality of separate microprocessors, application specific integrated circuits (ASIC), or the like. Furthermore, one or more of the microprocessors 139 may include multiple cores for concurrently processing a plurality of data streams.

The CPLD 141 may act as a watchdog to the main processor 139 and the DSP 143 and may flash the LCD 111 and brain state indicators 101 if an error is detected in the DSP 143 or main processor 139. Finally, the CPLD 141 controls the reset lines for the main microprocessor 139 and DSP 143.

A telemetry circuit 147 and antenna may be disposed in the PAD 10 to facilitate one-way or two-way data communication with the implanted device. The telemetry circuit 147 may be an off the shelf circuit or a custom manufactured circuit. Data signals received from the implanted device by the telemetry circuit 147 may thereafter be transmitted to at least one of the DSP 143 and the main processor 139 for further processing.

The DSP 143 and DRAM 145 receive the incoming data stream from the telemetry circuit 147 and/or the incoming data stream from the main processor 139. The brain state algorithms process the data (for example, EEG data) and estimate the subject's brain state, and are preferably executed by the DSP 143 in the PAD. In other embodiments, however, the brain state algorithms may be implemented in the implanted device, and the DSP may be used to generate the communication to the subject based on the data signal from the algorithms in the implanted device.

The main processor 139 is also in communication with the data storage device 151. The data storage device 151 preferably has at least about 7 GB of memory so as to be able to store data from about 8 channels at a sampling rate of between about 200 Hz and about 1000 Hz. With such parameters, it is estimated that the 7 GB of memory will be able to store at least about 1 week of subject data. Of course, as the parameters (e.g., number of channels, sampling rate, etc.) of the data monitoring change, so will the length of recording that may be achieved by the data storage device 151. Furthermore, as memory capacity increases, it is contemplated that the data storage device will be larger (e.g., 10 GB or more, 20 GB or more, 50 GB or more, 100 GB or more, etc.). Examples of some useful types of data storage device include a removable secure digital card or a USB flash key, preferably with a secure data format.

"Subject data" may include one or more of raw analog or digital EEG signals, compressed and/or encrypted EEG signals or other physiological signals, extracted features from the signals, classification outputs from the algorithms, etc. The data storage device 151 can be removed when full and read in card reader 157 associated with the subject's computer and/or the physician's computer. If the data card is full, (1) the subsequent data may overwrite the earliest stored data or (2) the subsequent data may be processed by the DSP 143 to estimate the subject's brain state (but not stored on the data card). While preferred embodiments of the data storage device 151 are removable, other embodiments of the data storage device may comprise a non-removable memory, such as FLASH memory, a hard drive, a microdrive, or other conventional or proprietary memory technology. Data retrieval off of such data storage devices 151 may be carried out through conventional wired or wireless transfer methods.

The power source used by the external assembly may comprise any type of conventional or proprietary power source, such as a non-rechargeable or rechargeable battery 155. If a rechargeable battery is used, the battery is typically a medical grade battery of chemistries such as a lithium polymer (LiPo), lithium ion (Li-Ion), or the like. The rechargeable battery 155 will be used to provide the power to the various components of the external assembly through a power bus (not shown). The main processor 139 may be configured to control the charge circuit 153 that controls recharging of the battery 155.

In addition to being able to communicate with the implanted device, the external assembly may have the ability to communicate wirelessly with a remote device—such as a server, database, physician's computer, manufacturer's computer, or a caregiver advisory device (all of which can be herein referred to as "CAD"). In the exemplary embodiment, the external assembly may comprise a communication assembly (not shown) in communication with the main processor 139 that facilitates the wireless communication with the remote device. The communication assembly may be a conventional component that is able to access a wireless cellular network, pager network, wifi network, or the like, so as to be able to communicate with the remote device. The wireless signal could be transfer of data, an instant message, an email, a phone call, or the like.

In one particular embodiment, the external assembly is able to deliver a signal through the communication assembly that is received by the CAD so as to inform the caregiver of the subject's brain state or change in brain state. The CAD would allow the caregiver to be away from the subject (and give the subject independence), while still allowing the caregiver to monitor the subject's brain state and susceptibility for seizure. Thus, if the subject's brain state indicates a high susceptibility for a seizure or the occurrence of a seizure, the caregiver would be notified via the CAD, and the caregiver could facilitate an appropriate treatment to the subject (e.g., small dosage of an antiepileptic drug, make the subject safe, etc.). A signal may be provided to the caregiver only if the subject has a high susceptibility for a seizure or if a seizure is detected, or it may provide the same indications that are provided to the subject.

In yet other embodiments, the communication assembly could be used to inform the caregiver that there is a communication error between the subject's implanted assembly and external assembly, so as to indicate that the subject is not being properly monitored and advised. Such a communication would allow the caregiver to intervene and/or inform the subject that they are not being monitored.

In other embodiments, the communication assembly could be used to facilitate either real-time or non-real time data transfer to the remote server or database. If there is real time transfer of data, such a configuration could allow for remote monitoring of the subject's brain state and/or EEG signals. Non-real time transfer of data could expedite transfer and analysis of the subject's recorded EEG data, extracted features, or the like. Thus, instead of waiting to upload the brain activity data from the subject's data storage device, when the subject visits their physician, the physician may have already had the opportunity to review and analyze the subject's transferred brain activity data prior to the subject's visit.

The external assembly may be configured to perform a self hardware/software test to detect system errors—such as power failures, software failures, impedance change, battery health of the implanted device and external assembly, internal clock and voltage reference, hardware (processors, memory, and firmware) checks, or the like. The self test may be performed periodically, upon initial startup, upon a system reset, or some combination thereof. The system preferably runs a self-test on the external assembly, implanted device, electrode array and the communication links. The external assembly may emit a tone and/or display information on the LCD at the initiation of the self-test(s). If the external assembly, implanted device, electrode array and/or communication link pass the self-test, the subject may be notified with an alert indicating the respective devices passed the self-test. If any of the components do not pass the self-test, the subject can be alerted with an output that indicates which component did not pass (for example, an icon on the LCD representing the component which did not pass the test flashes). There may also be an audio alert, such as a voice alert, that one or some of the devices failed the test. The external assembly may also indicate these failures with information or alert light 109 (FIG. 7). The system may then wait for input from the subject to acknowledge the system failure(s) by depressing a button on the external assembly (such as the "OK" button 135 in FIG. 6), which indicates the user is aware of the alert. Additionally or alternatively, there may be a text display on the LCD notifying the subject to contact the manufacturer or physician to receive further instructions.

The external assembly may be configured to be toggled between two or more different modes of operation. In one embodiment, the physician may toggle the external assembly between three different modes of operations. Of course, it should be appreciated that the external assembly may have as little as one mode of operation, or more than three different modes of operations.

In one example, a first mode of operation of the external assembly may be merely data collection, in which data signals from the implanted device are stored in the data storage 151 of the external assembly. In such a mode, the user interface 72 may be modified to only provide system status indications to the subject via the LCD 111, and the brain state indicators 101 may be temporarily disabled.

In a second mode of operation, after the brain state algorithms have been trained on the subject's data that was collected during the first mode of operation, the brain state algorithms may be implemented to process substantially real-time data signals and the brain state indicators 101 may be enabled so as to inform the subject of their substantially real-time brain state.

In a third mode of operation, it may be desirable to only receive and process the data signals from the implanted device, but no longer store the substantially continuous data signals in a memory of the external assembly. For example, if the brain state algorithms are performing as desired, the brain data signals from the implanted device will not have to be stored and analyzed. Consequently, the subject would not have to periodically replace the data card as frequently. However, it may still be desirable to store the data signals that immediately precede and follow any detected seizure. Consequently, in the third mode such seizure data signals may optionally be stored.

As noted above, in some embodiments the system comprises one or more brain state algorithms. In one embodiment, the brain state algorithms embodied in the present invention will generally characterize the subject's brain state as either "Low Susceptibility," "Unknown," "Elevated Susceptibility" or "Detection." It is intended that these are meant to be exemplary categories and are in no way to be limiting and additional brain states or fewer brain state indicators may be provided. There may be different types of algorithms which are configured to characterize the brain state into more or less discrete states. "Contra-ictal" generally means that brain activity indicates that the subject has a low susceptibility to transition to an ictal state and/or a pro-ictal state for an upcoming period of time (for example, 60 minutes to 90 minutes). This is considered positive information and no user lifestyle action is required. A pro-ictal state generally means that the algorithm(s) in the PAD are determining that the subject has an elevated susceptibility for a seizure (possibly within a specified time period). A "detection" state generally means that brain activity indicates that the subject has already transitioned into an ictal state (e.g., occurrence of an electrographic seizure) or that there is an imminent clinical seizure. User actions should be focused on safety and comfort. An "unknown" state generally means the current type of brain activity being monitored does not fit within the known boundaries of the algorithms and/or that the brain activity does not fit within the contra-ictal state, pro-ictal state, or ictal state. Therefore no evaluation can be reliably made. "Unknown" can also indicate there has been a change in the status of the brain activity and while the subject does not have an elevated susceptibility and no seizure has been detected, it is not possible to reliable tell the subject that they may not transition into an ictal state and/or pro-ictal state for a period of time. This state is considered cautionary and requires some cautionary action such as limiting exposure to risk. The two different types of "unknown" may have separate brain state indicators, or they may be combined into a single brain state indicator, or the user interface may not provide the "unknown" state to the subject at all.

The external assembly preferably comprises visual indicators, such as LEDs, notifying the subject of the determined brain state. In one preferred embodiments, the visual indicators for the brain state alerts will comprise a green, yellow/blue, and red lights. The green light will be illuminated when the PAD determines that the brain state is in a "low susceptibility to seizure" state. The yellow or blue light will be illuminated when the subject is in an "unknown" state. The PAD will emit a solid red light when the subject is in the "high susceptibility" state. The PAD will emit a blinking red light when the subject is in the "detection" state. The light colors or number of light indicators are not intended to be limiting. Any color may be used. It may be desirable to include additional lights or colors (e.g., orange) to further delineate the subject's estimated condition. In yet other embodiments, it may be desirable to display only a green light and red light.

Further exemplary details of external assembly 20 can be found in U.S. Provisional Application No. 60/952,463, filed Jul. 27, 2007, the disclosure of which is incorporated by reference herein in its entirety.

Figure 9:
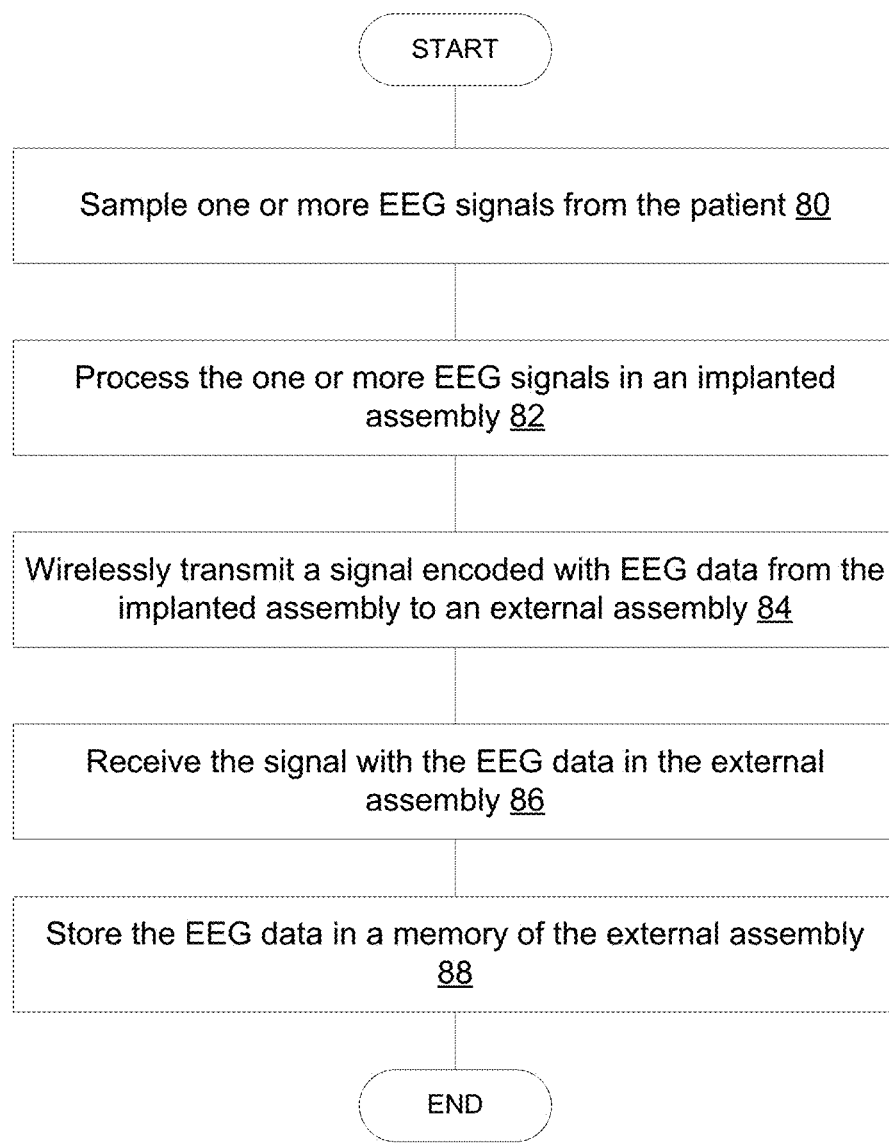
FIG. 9 is a simplified flow chart that illustrates one method of storing EEG data.

FIG. 9 illustrates an exemplary simplified method embodied by the present invention. In use, the implantable assembly 14 samples the brain activity signals with the active contacts on the electrode array 12 (step 80). The sampled brain activity signals are transmitted to the implantable assembly 14 over leads 16 (but this can also be done wirelessly). The implantable assembly 14 may then pre-process the sampled brain activity signals as desired (step 82), and then use the communication sub-assembly to transmit a substantially continuous wireless RF signal to the external assembly 20 that is encoded with EEG data (step 84). The RF signal emitted by the internal assembly 14 is received by an antenna in the external assembly, and the RF signal is decoded to extract the EEG data (step 86). The sampled EEG data may thereafter be stored in a memory of the external assembly 20 (step 88). Rather than storing the data in a memory in the external assembly (step 88), the data can also be transmitted to a remote device in substantial real time without storage in the external assembly.

In preferred embodiments, the wireless signal is transmitted substantially immediately after sampling of the EEG signal to allow for substantially continuous real-time transfer of the subject's EEG data to the external assembly 20. In alternate embodiments, however, the RF signal with the encoded EEG data may be temporarily buffered in an internal memory 52 (FIG. 4) of the implanted assembly 14 and the communication transmission to the external assembly 20 may be delayed by any desired time period and such transmissions may include the buffered EEG data and/or a real-time sampled EEG data.

Instead of sending large packets of stored data with each RF communication transmission, the methods and devices of the present invention substantially continuously sample physiological signals from the subject and communicate in real-time small bits of data during each RF signal communication to the external assembly. Of course, for embodiments in which real-time data transfer is not needed, it may be desirable to transmit larger packets of data to the external assembly 20 using the communication link, and such a communication protocol is also encompassed by the present invention.

As noted above, the data signals that are wirelessly transmitted from implanted assembly 14 may be encrypted so as to help ensure the privacy of the subject's data prior to transmission to the external assembly 20. Alternatively, the data signals may be transmitted to the external assembly 20 with unencrypted EEG data, and the EEG data may be encrypted prior to the storage of the EEG data in the memory of external assembly 20 or prior to transfer of the stored EEG data to the local computer workstation 22 or remote server 26.

The download of brain activity data may be manually carried out by the subject or automatically initiated by a component of system 10. After a time period of collecting EEG data (e.g., one day to one week, one week to two weeks, two weeks to one month, etc.), the external assembly 20 may be manually put in communication with a local computer workstation 22 through either a wireless link or wired link to download the stored data to a memory of the local computer workstation 22. For example, in one embodiment, a wired USB 2.0 connection (improvements thereof or other conventional interface) may be used to upload the stored EEG data to the local computer workstation 22. Alternatively, instead of downloading the data directly to a local or remote computer workstation 22, 26, the data may be downloaded to a portable hard drive or flash drive for temporary storage. In such embodiments, the drive may thereafter be brought or delivered into the physician's office for download and analysis.

Furthermore, as shown in FIG. 1, the communication sub-assembly of external assembly 20 may have the capability to continuously or periodically communicate wirelessly with a broadband, high speed communication network 24—such as a cellular network, pager network, the Internet (Wifi, WiMAX), or the like, to automatically and wirelessly transmit the stored and/or real-time data over the network 24 to a remote server (not shown) or remote computer workstation 26.

For example, the local computer workstation 22 (or remote computer workstation 26) may periodically command the external assembly to upload the data from the memory of the external assembly, or the external assembly may be programmed to automatically upload the EEG data according to a predetermined schedule or upon reaching a threshold level memory usage. By incrementally downloading days or weeks of stored brain activity data periodically, the subject's physician may be able to start analysis of the brain activity data and possibly complete the analysis of the long term data prior to the subject going to the physician's office. If a subject were to bring in a week or month of stored brain activity data for analysis by the physician, the subject would have to wait hours, days or even weeks for the analysis of the data to be completed. Consequently, instead of waiting for the analysis, analysis of the data may be substantially completed and therapy or diagnosis decisions may be made prior to the office visit and the subject would be able to immediately implement any changes or start therapy immediately after visiting the office.

Figure 10:
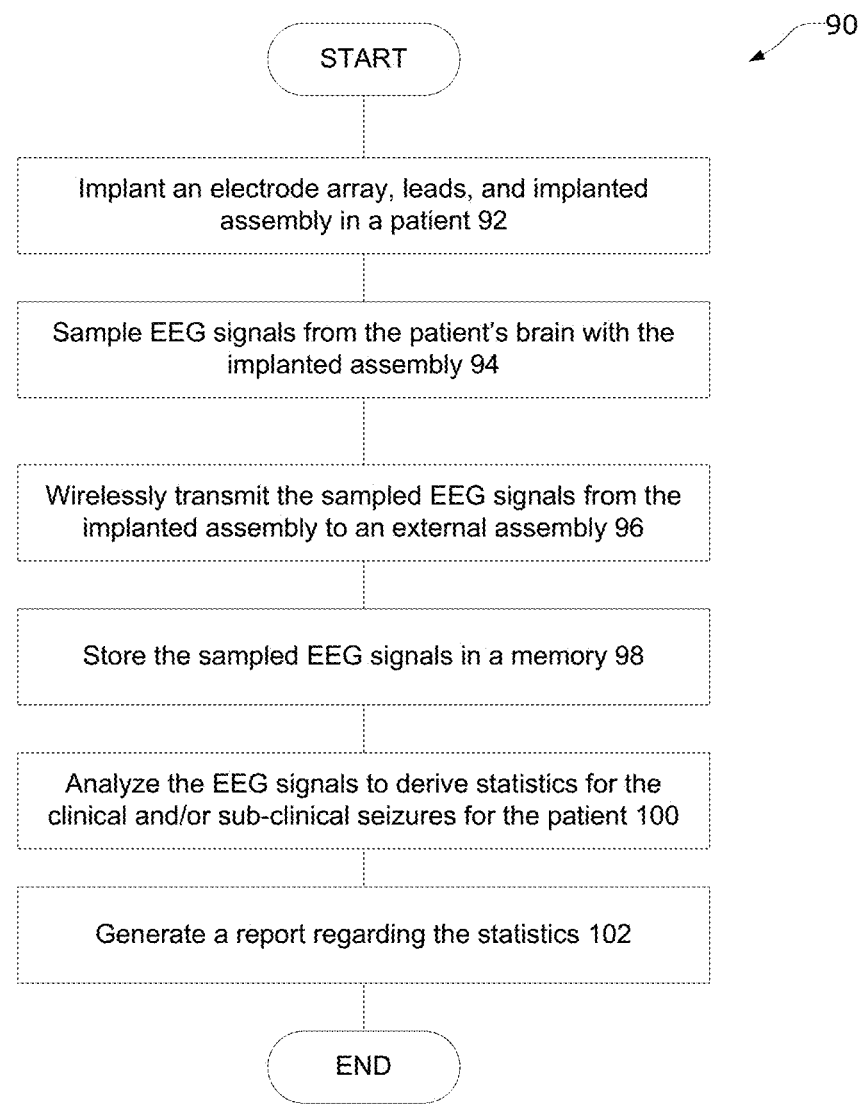
FIG. 10 illustrates a method of measuring seizure activity data for clinical and/or sub-clinical seizures.

Once implanted in the subject, the systems 10 of the present invention may be used for a variety of different data collection and monitoring purposes. For example, in one usage the systems of the present invention may be used to quantify seizure activity statistics for the subject. Currently, the most common method of quantifying a subject's seizure activity is through subject self reporting using a seizure diary. However, it has been estimated that up to 63% of all seizures are missed by subjects. Subject's missing the seizures are usually caused by the subjects being amnesic to the seizures, unaware of the seizures, mentally incapacitated, the seizures occur during sleep, or the like. FIG. 10 illustrates a simplified method 90 of measuring a subject's seizure activity statistics. At step 92, the electrode arrays 12, leads 16 (or can be wireless), and implanted assembly 14 are implanted in the subject. At step 94, the implanted assembly is activated to substantially continuously sample EEG signals from the subject. At step 96, the sampled EEG signals are wirelessly transmitted from the implanted assembly 14 to an external assembly 20. At step 98, the sampled EEG signals are stored in a memory—either in the external assembly 20 or in one of the computer workstations 22, 26. At step 100, the stored EEG signals are manually analyzed by the physician and/or analyzed with EEG analysis software, typically using a seizure advisory algorithm(s) or spike detector, to derive statistics for the clinical seizures and/or the sub-clinical seizures for the subject based on the long-term, ambulatory EEG data. For example, the following statistics may be quantified using the present invention:

Seizure count over a time period—How many clinical and sub-clinical seizures does the subject have in a specific time period?

Seizure frequency—How frequent does the subject have seizures? What is the seizure frequency without medication and with medication? Without electrical stimulation and with electrical stimulation?

Seizure duration—How long do the seizures last? Without medication and with medication? Without electrical stimulation and with electrical stimulation?

Seizure timing—When did the subject have the seizure? Do the seizures occur more frequently at certain times of the day?

Seizure patterns—Is there a pattern to the subject's seizures? After certain activities are performed? What activities appear to trigger seizures for this particular subject?

Finally, at step 102, report generation software may be used to generate a report based on the statistics for the seizure activity. The report may include some or all of the statistics described above, and may also include the EEG signal(s) associated with one or more of the seizures. The report may include text, graphs, charts, images, or a combination thereof so as to present the information to the physician and/or subject in an actionable format.

As noted above, the present invention enables the quantification, documentation and long term monitoring of sub-clinical seizures in a subject. Because the subject is unaware of the occurrence of sub-clinical seizures, heretofore the long term monitoring of sub-clinical seizures was not possible. Documentation of the sub-clinical seizures may further provide insight into the relationship between sub-clinical seizures and clinical seizures, may provide important additional information relevant to the effectiveness of subject therapy, and may further enhance the development of additional treatments for epilepsy.

Figure 11:
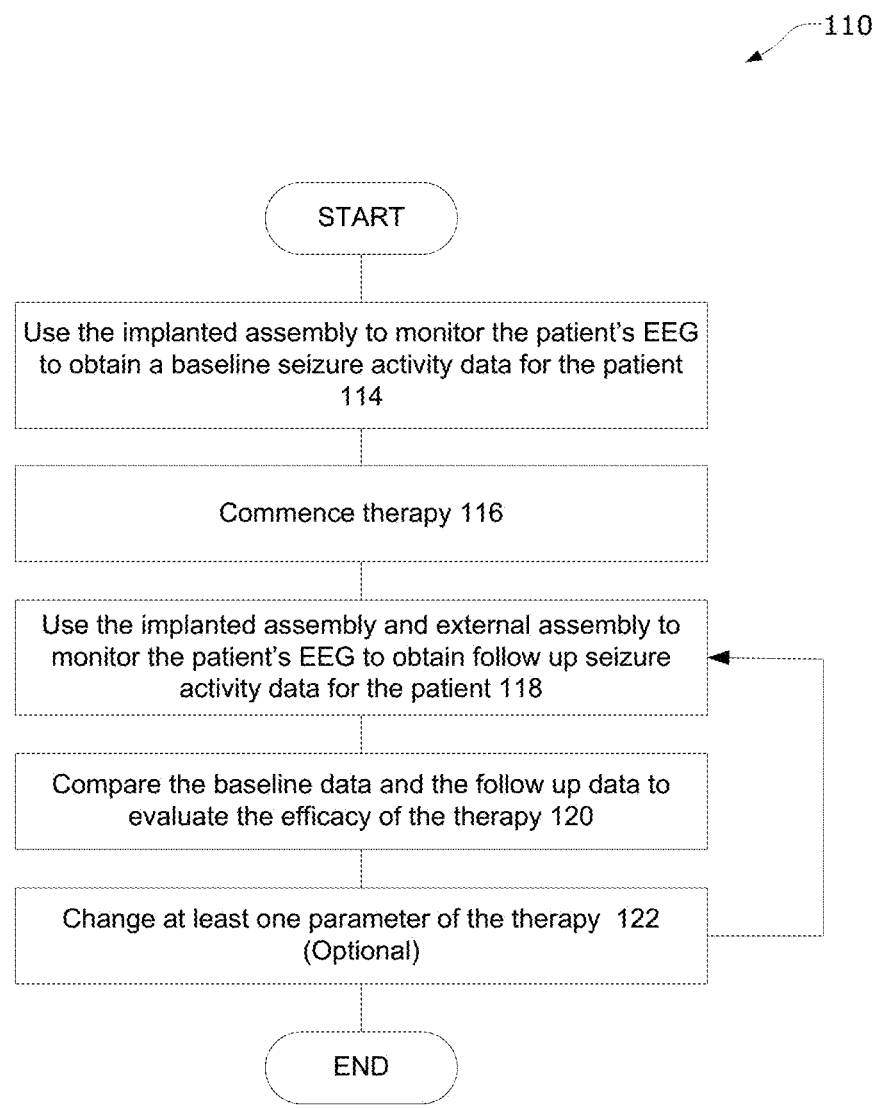
FIG. 11 illustrates a method of evaluating efficacy of a therapy.

FIG. 11 illustrates one exemplary method of how the seizure activity data may be used to evaluate the efficacy or clinical benefit of a current or potential therapy and allow for the intelligent selection of an appropriate therapy for an individual subject or stopping the usage of ineffective therapies. Currently, effectiveness of the AED therapy is based on self-reporting of the subject, in which the subject makes entries in a diary regarding the occurrence of their seizure(s). If the entries in the subject diary indicate a reduction in seizure frequency, the AED is deemed to be effective and the subject continues with some form of the current regimen of AEDs. If the subject entries in the subject diary do not indicate a change in seizure frequency, the AEDs are deemed to be ineffective, and typically another AED is prescribed—and most often in addition to the AED that was deemed to be ineffective. Because AEDs are typically powerful neural suppressants and are associated with undesirable side-effects, the current methodology of assessing the efficacy of the AEDs often keeps the subject on ineffective AEDs and exposes the subject to unnecessary side-effects.

By way of example, a medically refractory subject coming to an epilepsy center for the first time might first have the system of the present invention implanted and then asked to collect data for a prescribed time period, e.g., 30 days. The initial 30 days could be used to establish a baseline measurement for future reference. The physician could then prescribe an adjustment to the subject's medications and have the subject collect data for another time period, e.g., an additional 30 day period. Metrics from this analysis could then be compared to the previous analysis to see if the adjustment to the medications resulted in an improvement. If the improvement was not satisfactory, the subject can be taken off of the unsatisfactory medication, and a new medication could be tried. This process could continue until a satisfactory level of seizure control was achieved. The present invention provides a metric that allows physicians and subjects to make informed decisions on the effectiveness and non-effectiveness of the medications.

FIG. 11 schematically illustrates this method 110. At step 114, the implantable assembly and external assembly are used to monitor the subject's EEG to obtain a baseline measurement for the subject. The baseline measurement is typically seizure activity statistics for a specific time period (e.g., number of seizures, seizure duration, seizure pattern, seizure frequency, etc.). It should be appreciated however, that the baseline measurement may include any number of types of metrics. For example, the baseline metric may include univariate, bivariate, or multivariate features that are extracted from the EEG, or the like. In one preferred embodiment, the baseline measurement is performed while the subject is not taking any AEDs or using any other therapy. In other embodiments, however, the subject may be taking one or more AEDs and the baseline measurement will be used to evaluate adjustments to dosage or other add-on therapies.

At step 116, the therapy that is to be evaluated is commenced. The therapy will typically be an AED and the subject will typically have instructions from the neurologist, epileptologist, or drug-manufacturer regarding the treatment regimen for the AED. The treatment regimen may be constant (e.g., one pill a day) throughout the evaluation period, or the treatment regimen may call for varying of some parameter of the therapy (e.g., three pills a day for the first week, two pills a day for the second week, one pill a day for the third week, etc.) during the evaluation period. During the evaluation period, the implantable assembly and external assembly will be used to substantially continuously sample the subject's EEG. The sampled EEG may thereafter be processed to obtain a follow-up measurement for the subject (Step 118). If the baseline measurement was seizure statistics for the baseline time period, then the follow-up measurement will be the corresponding seizure statistics for the evaluation period. At step 120, the baseline measurement is compared to the follow-up measurement to evaluate the therapy. If the comparison indicates that the therapy did not significantly change the subject's baseline, the therapy may be stopped, and other therapies may be tried.

Currently, the primary metric in evaluating the efficacy of an AED is whether or not the AED reduces the subject's seizure count. In addition to seizure count, the systems of the present invention would be able to track any reduction in seizure duration, modification in seizure patterns, reduction in seizure frequency, or the like. While seizure count is important, because the present invention is able to provide much greater detail than just seizure count, efficacy of an AED may be measured using a combination of additional metrics, if desired. For example, if the subject was having a large number of sub-clinical seizures, spike bursts, or other epileptiform activity (which the subject was not aware of) and the AED was effective in reducing or stopping the sub-clinical seizures, the systems of the present invention would be able to provide metrics for such a situation. With conventional subject diary "metrics", the subject and physician would not be aware of such a reduction, and such an AED would be determined to be non-efficacious for the subject. However, because the present invention is able to provide metrics for the sub-clinical seizures, the efficacious medication could be continued.

At step 122, the epileptologist or neurologist may decide to change one or more parameters of the therapy. For example, they may change a dosage, frequency of dosage, form of the therapy or the like, and thereafter repeat the follow-up analysis for the therapy with the changed parameter. After the "second" follow up measurement is complete, the second follow up data may be obtained and thereafter compared to the "first" follow up measurements and/or the baseline measurements.

Of course, the therapy is not limited to AED therapy. Therapies that can be assessed by the present invention can include cooling therapy, electrical stimulation (such as vagus nerve stimulation, deep brain stimulation, cortical stimulation), or the like. The present invention may be used to screen the subject's for determining appropriate therapy for their condition and/or to determine the appropriate parameters for the selected therapy.

Figure 12:
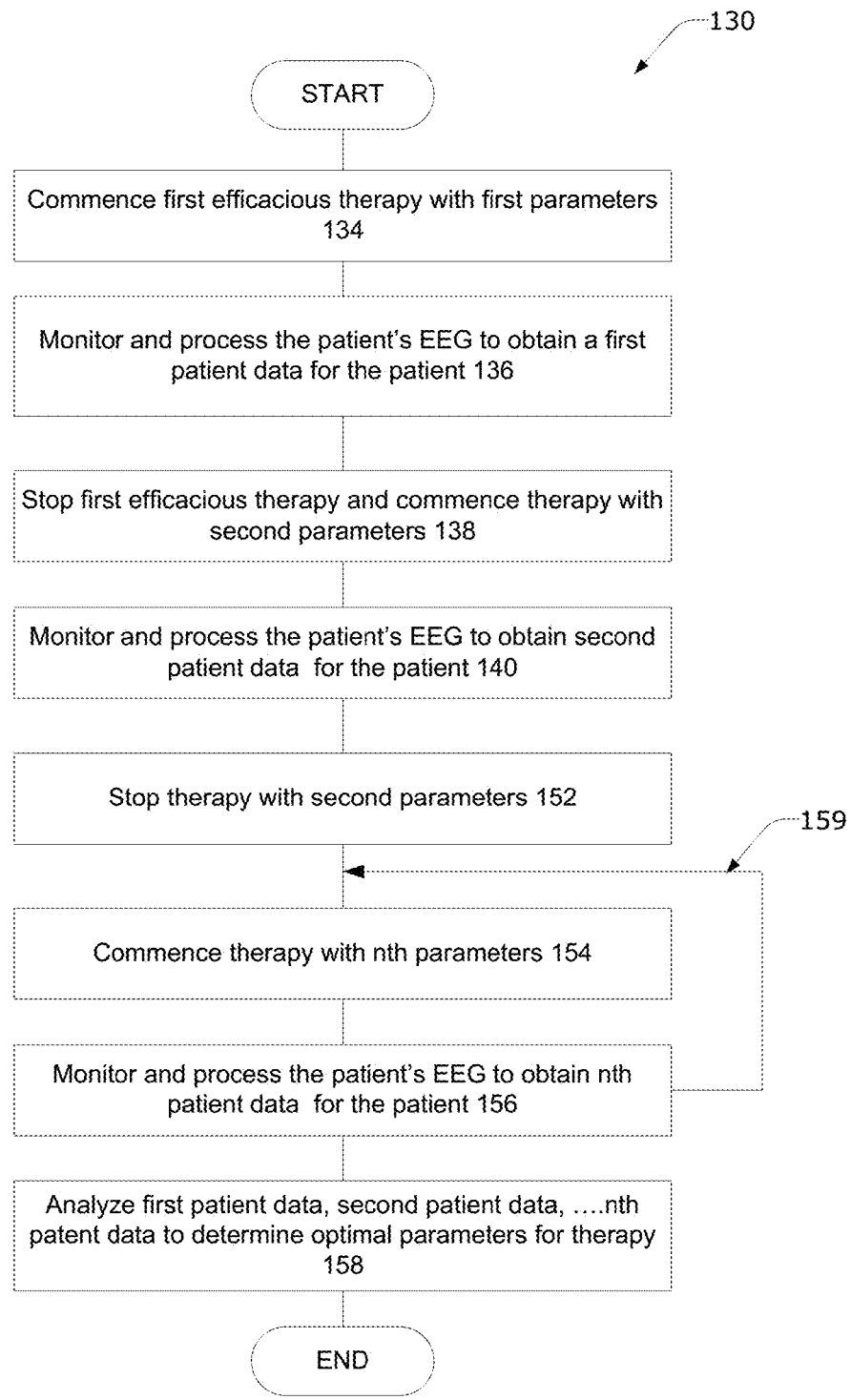
FIG. 12 illustrates a method of titrating an efficacious therapy.

In addition to evaluating an efficacy of a therapy for an individual subject, the metrics that are provided by the present invention also enable an intelligent titration of a subject's medications. As shown in FIG. 12, if the subject is on a treatment regimen of an efficacious therapy, the present invention may be used to reduce/titrate a dosage or frequency of intake of the AED (or AEDs) 130. Typically, the subject will already be on a treatment regimen of the efficacious therapy, but if not, the efficacious therapy is commenced with the prescribed parameters, e.g., "standard" dosage (Step 134). At step 136, the subject's EEG (and/or other physiological signal) is monitored for a desired time period to obtain a first subject data measurement for the subject (e.g., the baseline measurement). Similar to previous embodiments, the first subject data measurement may be any desired metrics, but will typically be selected from clinical seizure frequency, clinical seizure duration, sub-clinical seizure frequency, sub-clinical seizure duration, medication side effects. At step 138, after the baseline measurement has been taken, the first efficacious therapy is stopped and a therapy with at least one changed parameter is started (referred to as "therapy with second parameters" in FIG. 12). Typically, the changed parameter will be a reduction in dosage, but it could be changing a frequency of the same dosage, a change in formulation or form of the same AED, or the like.

At step 140, the subject's EEG is monitored and processed to obtain a second subject data measurement for the subject (e.g., follow-up data measurement). If the neurologist or epileptologist is satisfied with the results, the titration may end. But in many embodiments, the titration process will require more than one modification of parameters of the therapy. In such embodiments, the second therapy is stopped (step 142), and a therapy with $N^{th}$ parameters (e.g., third, fourth, fifth . . . ) is commenced (step 144). Monitoring and processing of the subject's EEG signals are repeated (step 146), and the process is repeated a desired number of times (as illustrated by arrow 147). Once the desired numbers of modifications to the therapy have been made, the various subject data measurements may be analyzed and compared to each other to determine the most desirous parameters for the therapy (step 148).

With the instrumentation provided by the present invention, the process of selecting appropriate AEDs and the dosages of such AEDs could occur much faster and with much greater insight than ever before. Further, the chance of a subject remaining on an incremental AED that was providing little incremental benefit would be minimized. Once a subject was under control, the subject could cease the use of the system, but the implantable assembly could remain. In the future, the subject might be asked to use the system again should their condition change.

In addition to or as an alternative to the above data collection uses, the systems 10 of the present invention may be used to analyze EEG data substantially in real-time and provide an output to the subject and/or provide a therapy to the subject based on the analysis of the EEG data. In preferred embodiments, the systems of the present invention may be used as seizure advisory systems that measure the subject's susceptibility to a seizure and/or to detect the onset of the seizure prior to the clinical manifestation of the seizure and provide an appropriate warning to the subject.

The platform of system 10 used for data collection (described above) and the system used for determining the subject's susceptibility for having a seizure will generally have the same general components, so that the same system may be used for both data collection and advising of susceptibility to seizure. However, when the system is used for data collection during a training period, the algorithms that determine the subject's susceptibility of having a seizure may be disabled or not yet programmed in the system so as to not be accessible to the subject. If and when seizure advising is desired, such algorithms may be enabled and/or added into the system.

For example, EEG data may be collected as noted above. The collected EEG data may be analyzed off-line (e.g., in a separate computer, such as workstation 22) and, if desired, algorithms may be customized or otherwise tuned to the subject specific EEG data. Thereafter, the parameters of the disabled algorithm(s) may be modified or the entire tuned algorithm may be uploaded to a memory of system 10 and the aspects of the system relevant to seizure advising may be enabled. Finally, the seizure advising functionality in the system 10 may be enabled and used by the subject in real-time on a substantially continuous basis.

Figure 13:
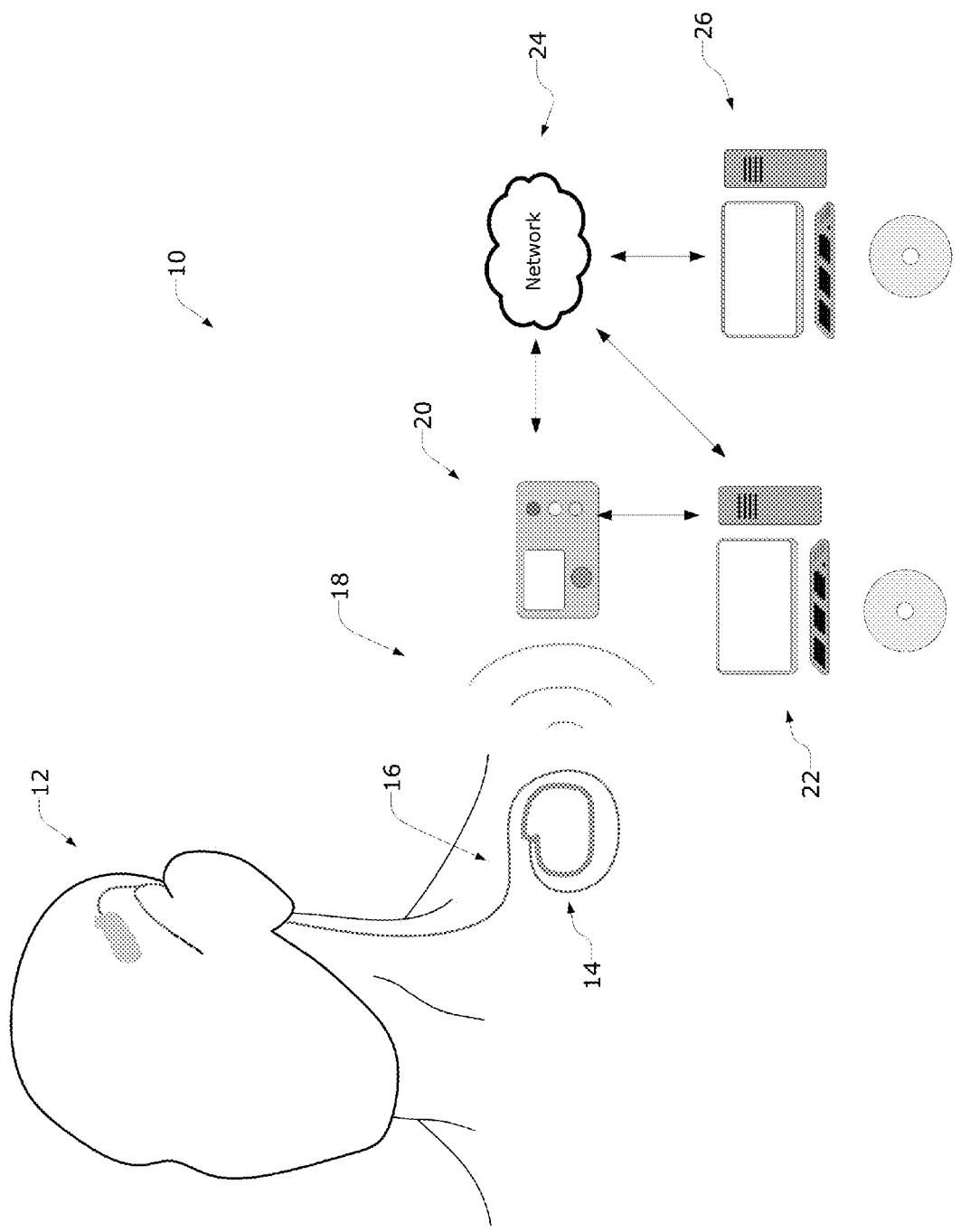
FIG. 13 illustrates one embodiment of a simplified seizure advisory system which comprises an array of epidural or subdural electrodes and an array of depth electrodes in communication with an external assembly through an implanted assembly.

FIG. 13 illustrates an embodiment of the seizure advisory system in which the electrode array 12 includes at least one depth electrode array, but otherwise contains similar components as the system of FIG. 1. Typically, the depth electrode will be only for sampling EEG signals, but as will be described below, the electrode arrays 12 may be used to deliver electrical stimulation directly to the brain. The system 10 shown in FIGS. 1 and 13 will include algorithms that process the EEG in substantially real-time to determine the subject's susceptibility for having a seizure. When a high susceptibility to a seizure is determined, a user interface of the external assembly 20 will provide an output to the subject that is indicative of the high susceptibility to the seizure. In the illustrated embodiment, the output to the subject may be a visual display on the LCD, a light display on the LED, a vibratory signal, and/or an audio output, etc., as described above.

Figure 14:
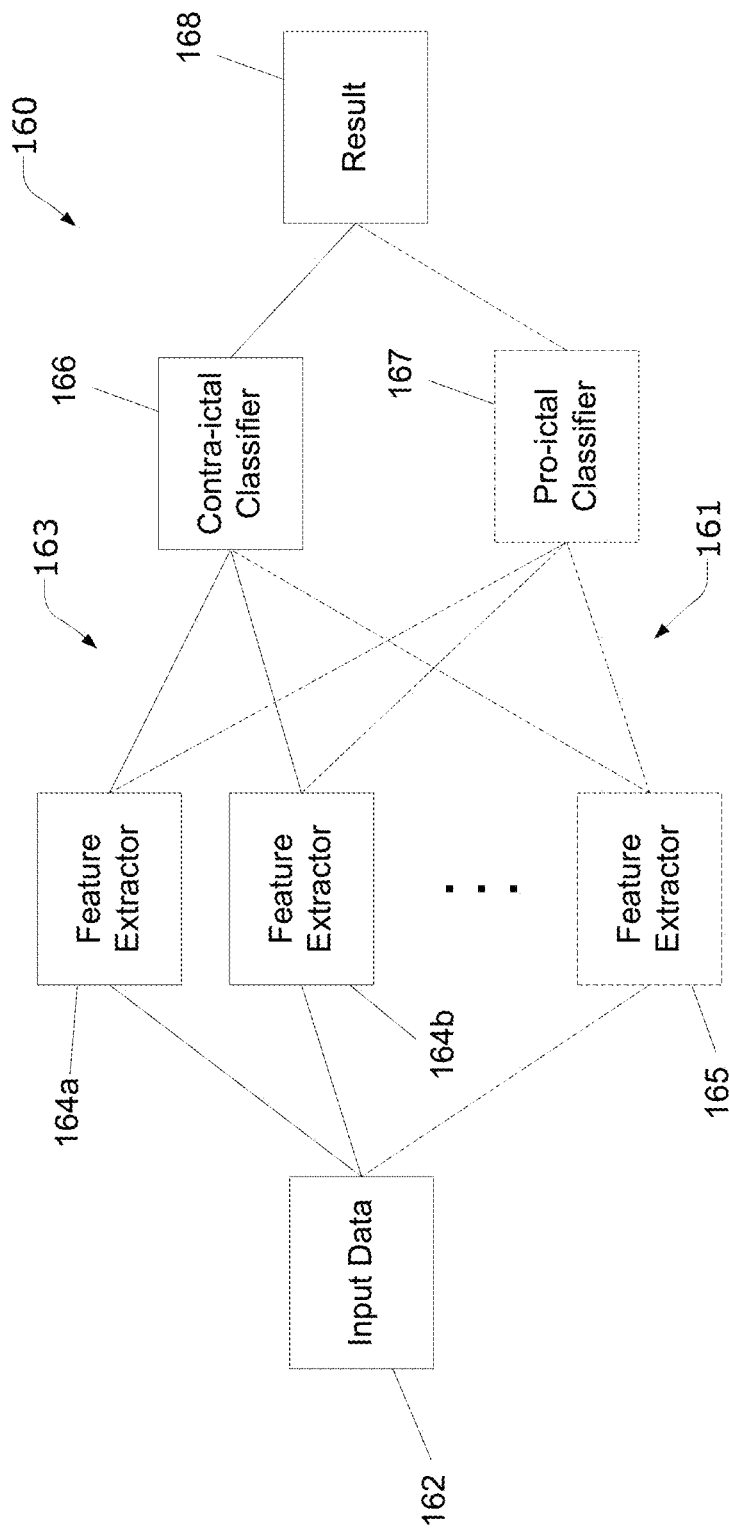
FIG. 14 schematically illustrates a plurality of algorithms that may be embodied by the present invention.

FIG. 14 depicts an example of the overall structure of a system for performing substantially real-time assessment of the subject's brain activity and for determining the communication output that is provided to the subject. The system may comprise one or more algorithms or modules that process input data 162. The algorithms may take a variety of different forms, but typically comprises one or more feature extractors 164a, 164b, 165 and at least one classifier 166 and 167. The embodiment illustrated in FIG. 14 shows a contra-ictal algorithm 163 and a pro-ictal algorithm 161 which share at least some of the same feature extractors 164a and 164b. In alternative embodiments, however, the algorithms used in the system may use exactly the same feature extractors or completely different feature extractors.

The input data 162 is typically EEG, but may comprise representations of physiological signals obtained from monitoring a subject and may comprise any one or combination of the aforementioned physiological signals from the subject. The input data may be in the form of analog signal data or digital signal data that has been converted by way of an analog to digital converter (not shown). The signals may also be amplified, preprocessed, and/or conditioned to filter out spurious signals or noise. For purposes of simplicity the input data of all of the preceding forms is referred to herein as input data 162. In one preferred embodiment, the input data comprises between about 1 channel and about 64 channels of EEG from the subject.

The input data 162 from the selected physiological signals is supplied to the one or more feature extractors 164a, 164b, 165. Feature extractor 164a, 164b, 165 may be, for example, a set of computer executable instructions stored on a computer readable medium, or a corresponding instantiated object or process that executes on a computing device. Certain feature extractors may also be implemented as programmable logic or as circuitry. In general, feature extractors 164a, 164b, 165 can process data 162 and identify some characteristic of interest in the data 162. Such a characteristic of the data is referred to herein as an extracted feature.

Each feature extractor 164a, 164b, 165 may be univariate (operating on a single input data channel), bivariate (operating on two data channels), or multivariate (operating on multiple data channels). Some examples of potentially useful characteristics to extract from signals for use in determining the subject's propensity for a neurological event, include but are not limited to, bandwidth limited power (alpha band [8-13 Hz], beta band [13-18 Hz], delta band [0.1-4 Hz], theta band [4-8 Hz], low beta band [12-15 Hz], mid-beta band [15-18 Hz], high beta band [18-30 Hz], gamma band [30-48 Hz], high frequency power [>48 Hz], bands with octave or half-octave spacings, wavelets, etc.), second, third and fourth (and higher) statistical moments of the EEG amplitudes or other features, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STL-max, T-index, angular frequency, and entropy), line length calculations, first, second and higher derivatives of amplitude or other features, integrals, and mathematical linear and non-linear operations including but not limited to addition, subtraction, division, multiplication and logarithmic operations. Of course, for other neurological conditions, additional or alternative characteristic extractors may be used with the systems described herein.

The extracted characteristics can be supplied to the one or more classifiers 166, 167. Like the feature extractors 164a, 164b, 165, each classifier 166, 167 may be, for example, a set of computer executable instructions stored on a computer readable medium or a corresponding instantiated object or process that executes on a computing device. Certain classifiers may also be implemented as programmable logic or as circuitry.

The classifiers 166, 167 analyze one or more of the extracted characteristics, and either alone or in combination with each other (and possibly other subject dependent parameters), provide a result 168 that may characterize, for example, a subject's condition. The output from the classifiers may then be used to determine the subject's susceptibility for having a seizure, which can determine the output communication that is provided to the subject regarding their condition. As described above, the classifiers 166, 167 are trained by exposing them to training measurement vectors, typically using supervised methods for known classes, e.g. ictal, and unsupervised methods as described above for classes that can't be identified a priori, e.g. contra-ictal. Some examples of classifiers include k-nearest neighbor ("KNN"), linear or non-linear regression, Bayesian, mixture models based on Gaussians or other basis functions, neural networks, and support vector machines ("SVM"). Each classifier 166, 167 may provide a variety of output results, such as a logical result or a weighted result. The classifiers 166, 167 may be customized for the individual subject and may be adapted to use only a subset of the characteristics that are most useful for the specific subject. Additionally, over time, the classifiers 166, 167 may be further adapted to the subject, based, for example, in part on the result of previous analyses and may reselect extracted characteristics that are used for the specific subject.

For the embodiment of FIG. 14, the pro-ictal classifier 167 may classify the outputs from feature extractors 164a, 164b to detect characteristics that indicate that the subject is at an elevated susceptibility for a neurological event, while the contra-ictal classifier 166 may classify the outputs from feature extractors 164a, 164b, 165 to detect characteristics that occur when the subject is unlikely to transition into an ictal condition for a specified period of time. The combined output of the classifiers 166, 167 may be used to determine the output communication provided to the subject. In embodiments which comprise only the contra-ictal algorithm, the output from the contra-ictal classifier 166 alone may be used to determine the output communication to the subject. Further details of exemplary algorithms that may be used to identify a subject's susceptibility to having a seizure may be found in U.S. Provisional Patent Application No. 60/897,549, filed Jan. 25, 2007, to Snyder et al., entitled "Systems and Methods for Identifying a Contra-ictal Condition in a Subject" and co-pending application Ser. No. 12/020,450, filed on Jan. 25, 2008, titled "Systems and Methods for Identifying a Contra-Ictal Condition in a Subject", the complete disclosures of which are incorporated herein by reference.

Depending on the specific feature extractors and classifiers used, the computational demands of the analysis provided by feature extractors 164a, 164b, 165 and classification provided by classifiers 166, 167 can be extensive. In the case of ambulatory systems supplied by portable power sources, such as batteries, supplying the power required to meet the computational demands can severely limit power source life. In preferred embodiments, both the seizure advisory algorithm are embodied in the external assembly 20. Processing the EEG data with the algorithms in the external assembly 20 provides a number of advantages over having the algorithms in the implanted assembly. First, keeping the processing in the external assembly 20 will reduce the overall power consumption in the implanted assembly 14 and will prolong the battery life of the implanted assembly 14. Second, charging of battery or replacing the battery of the external assembly 20 is much easier to accomplish. The battery of the external assembly may be charged by placing the external assembly 20 in a recharging cradle (e.g., inductive recharging) or simply by attaching the external assembly to an AC power source. Third, customizing, tuning and/or upgrading the algorithms will be easier to achieve in the external assembly 20. Such changes may be carried out by simply connecting the external assembly to the physician's computer workstation 20 and downloading the changes. Alternatively, upgrading may be performed automatically over a wireless connection with the communication sub-assembly 64.

While it is preferred to have the observer algorithms 160 in the external assembly 20, in alternate embodiments of the present invention, the observer algorithms 160 may be wholly embodied in the implanted assembly 14 or a portion of one or more of the observer algorithms 160 may be embodied in the implanted assembly 14 and another portion of the one or more algorithms may be embodied in the external assembly 20. In such embodiments, the processing sub-assembly 44 (or equivalent component) of the implanted assembly 14 may execute the analysis software, such as a seizure advisory algorithm(s) or portions of such algorithms. For example, in some configurations, one or more cores of the processing sub-assembly 44 may run one or more feature extractors that extract features from the EEG signal that are indicative of the subject's susceptibility to a seizure, while the classifier could run on a separate core of the processing sub-assembly 44. Once the feature(s) are extracted, the extracted feature(s) may be sent to the communication sub-assembly 46 for the wireless transmission to the external assembly 20 and/or store the extracted feature(s) in memory sub-system 52 of the implanted assembly 14. Because the transmission of the extracted features is likely to include less data than the EEG signal itself, such a configuration will likely reduce the bandwidth requirements for the wireless communication link 18 between the implantable assembly 14 and the external assembly 20.

In other embodiments, the seizure advisory algorithms may be wholly embodied within the implanted assembly 14 and the data transmission to the external assembly 29 may include the data output from the classifier, a warning signal, recommendation, or the like. A detailed discussion of various embodiments of the internal/external placement of such algorithms are described in commonly owned U.S. patent application Ser. No. 11/322,150, filed Dec. 28, 2005 to Bland et al., and U.S. Provisional Patent Application No. 60/805,710, filed Jun. 23, 2006, the complete disclosures of which are incorporated herein by reference.

Figure 15:
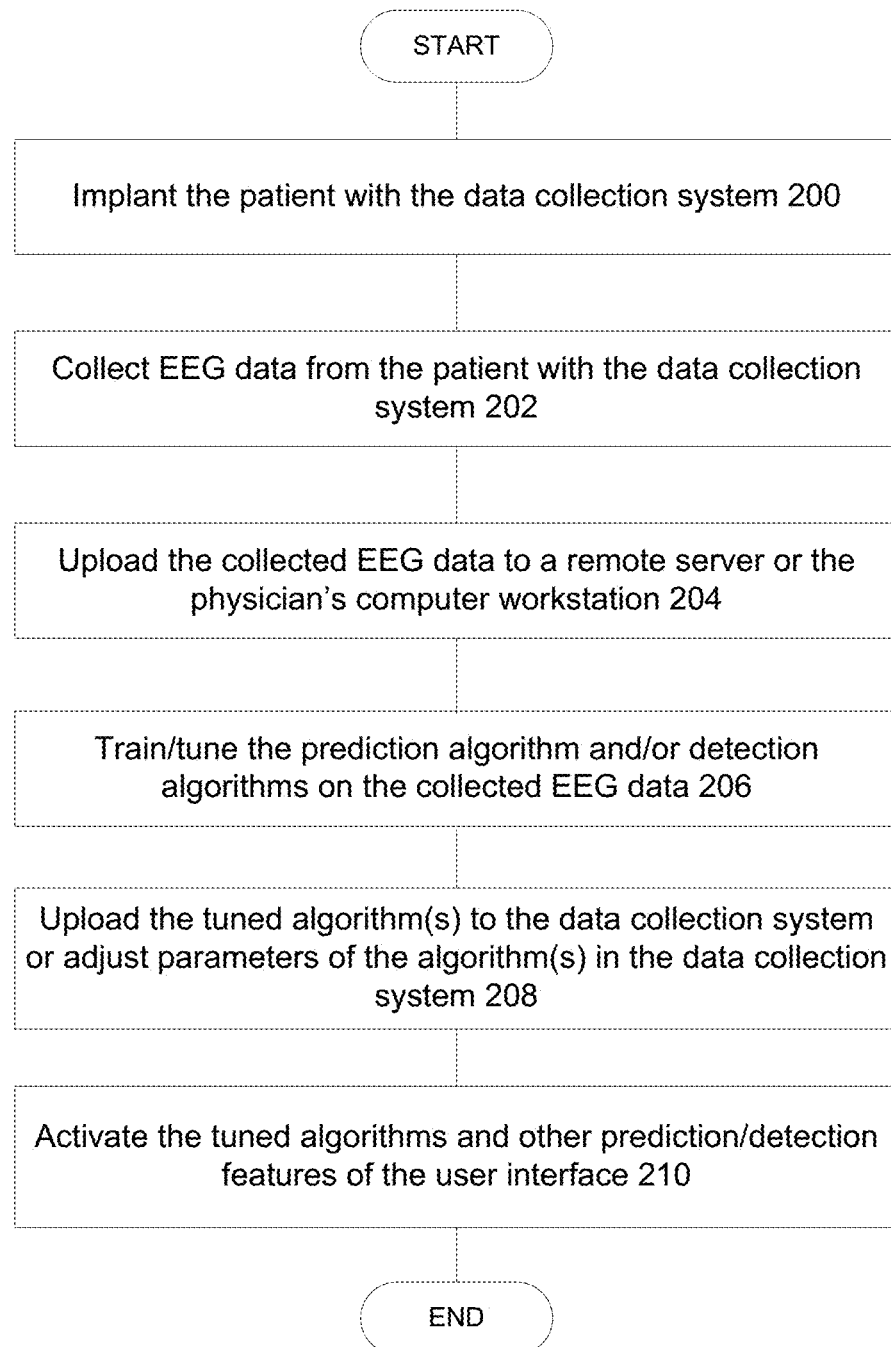
FIG. 15 illustrates a method of using a seizure advisory system.

FIG. 15 illustrates a method of using the systems described herein to collect data, tune the algorithms and use the tuned algorithms to estimate the subject's susceptibility to a seizure. At step 200, the subject is implanted with the system 10 in which the seizure advisory algorithms are disabled or not yet present in the system. The user interface aspects that are related to the seizure advising may also be disabled.

At step 202, the system is used to collect EEG data for a desired time period, as described in detail above. Generally, the desired time period will be a specified time period such as at least one week, between one week and two weeks, between two weeks and one month, between one month and two months, or two months or more. But the desired time period may simply be a minimum time period that provides a desired number of seizure events. At step 204, the collected EEG data may be periodically downloaded to the physician's computer workstation or the entire EEG data may be brought into the physician's office in a single visit.

At step 206, the physician may analyze the EEG data using the computer workstation that is running EEG analysis software, the EEG data may be transferred to a remote analyzing facility that comprises a multiplicity of computing nodes where the EEG data may be analyzed on an expedited basis, or it may even be possible to analyze the EEG analysis software in the external assembly 20. Analysis of the EEG data may be performed in a piecewise fashion after the shorter epochs of EEG data is uploaded to the database, or the analysis of the EEG data may be started after the EEG data for the entire desired time period has been collected. Typically, "analysis of the EEG data" will include identifying and annotating at least some of spike bursts, the earliest electrographic change (EEC), unequivocal electrical onset (UEO), unequivocal clinical onset (UCO), electrographic end of seizure (EES). Identification of such events may be performed automatically with a seizure detection algorithm, manually by board certified epileptologists, or a combination thereof. After the EEG data is annotated, the seizure advisory algorithm(s) may be trained on the annotated EEG data in order to tune the parameters of the algorithm(s) to the subject specific EEG data.

Once the algorithm(s) are tuned to meet minimum performance criteria, at step 208 the tuned algorithm(s) or the parameter changes to the base algorithm may be uploaded to the external assembly 20. At step 210, the tuned algorithm and the other user interface aspects of the present invention may be activated, and the observer algorithm may be used by the subject to monitor the subject's susceptibility to a seizure and/or detect seizures.

When the seizure advisory system 10 determines that the subject is at an increased susceptibility to a seizure (or otherwise detects a seizure), the external assembly may be configured to generate a seizure warning to the subject, as described above. For example, the external assembly may activate a red or yellow LED light, generate a visual warning on the LCD, provide an audio warning, deliver a tactile warning, or any combination thereof. If desired, the warning may be "graded" so as to indicate the confidence level of the seizure advisory, indicate the estimated time horizon until the seizure, or the like. "Grading" of the warning may be through generation of different lights, audio, or tactile warning or a different pattern of lights, audio or tactile warnings.

Additionally or alternatively, the external assembly may include an instruction to the subject regarding an appropriate therapy for preventing or reducing the susceptibility for the seizure. The instruction may instruct the subject to take a dosage of their prescribed AED, perform biofeedback to prevent/abort the seizure, manually activate an electrical stimulator (e.g., use a wand to activate an implanted VNS device) or merely to instruct the subject to make themselves safe. A more complete description of various instructions that may be output to the subject are described in commonly owned, copending U.S. patent application Ser. Nos. 11/321, 897 and 11/321,898, both of which are incorporated by reference herein.

The outputs provided to the subject via the external assembly may be a standardized warning or instruction, or it may be programmed by the physician to be customized specifically to the subject and their condition. For example, different subjects will be taking different AEDs, different dosages of the AEDs, and some may be implanted with manually actuatable stimulators (e.g., NeuroPace RNS, Cyberonics VNS, etc.), and the physician will likely be desirous to customize the therapy to the subject. Thus, the physician will be able to program the warning and/or instruction to correspond to the level of susceptibility, estimated time horizon to seizure, or the like.

Figure 16:
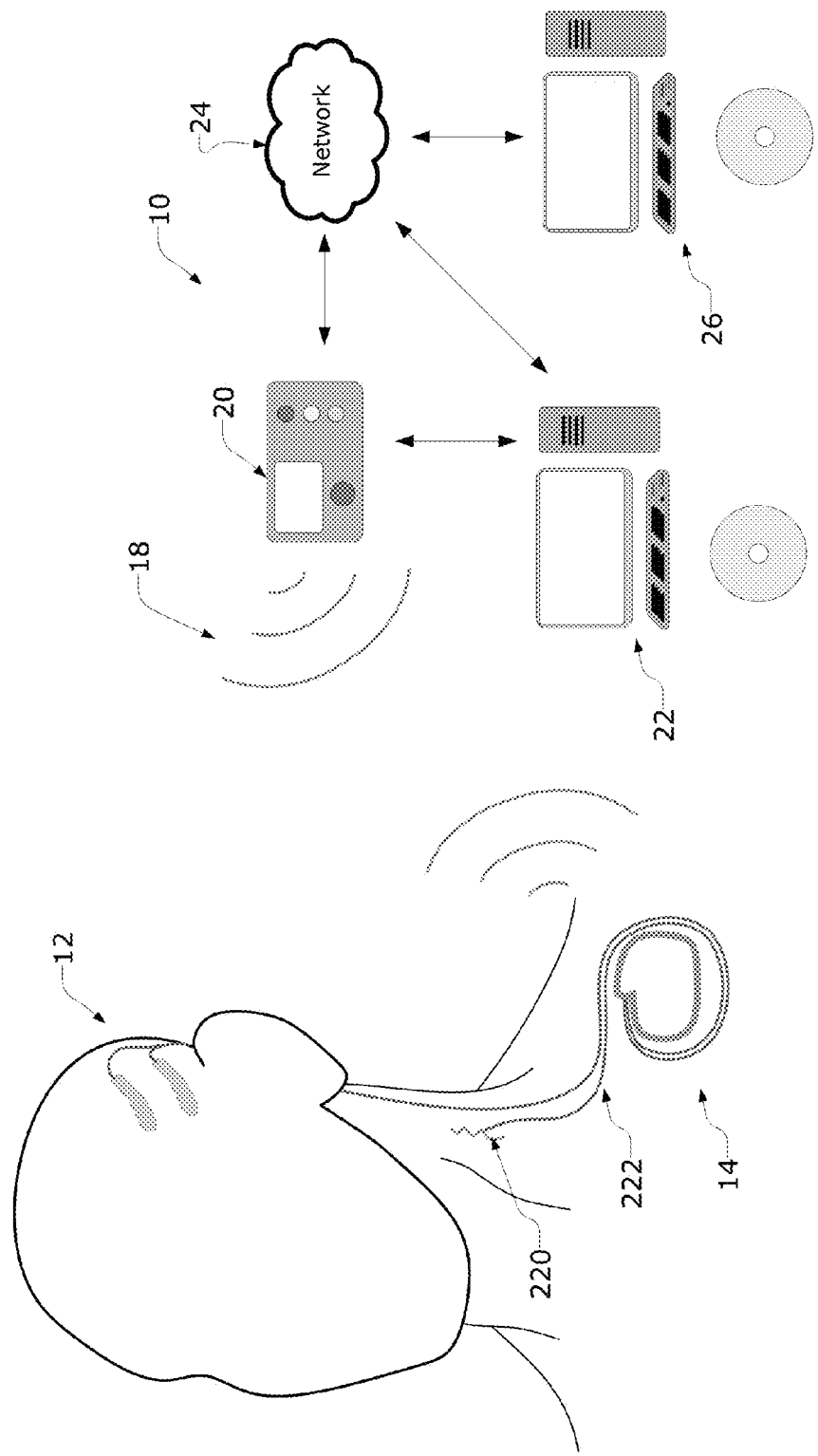
FIG. 16 illustrates another variation to the system of FIG. 6 which includes a pulse generator that is coupled to a vagus nerve electrode array.

The systems 10 of the present invention may also be adapted to provide closed-loop therapy to the subject. FIG. 16 illustrates one embodiment of the system 10 that includes therapy delivery assembly in the implanted assembly 14. The system 10 illustrated in FIG. 16 will generally have the same components as shown in FIGS. 1 and 13, but will also include an implanted pulse generator (not shown) that is in communication with a vagus nerve cuff electrode 220 via a lead 222. When the seizure advisory system determines that the subject is at an elevated susceptibility to a seizure, the system may automatically initiate delivery of electrical stimulation to the vagus nerve cuff electrode. The parameters (e.g., burst/no burst mode, amplitude, pulse width, pulse frequency, etc.) of the electrical stimulation may be varied based on the subject's susceptibility, or the parameter may be constant.

While not shown in FIG. 16, the present invention further embodies other therapy outputs—such as electrical stimulation of the brain tissue (e.g., deep brain structures, cortical stimulation) using electrode array 12 or other electrode arrays (not shown), stimulation of cranial nerves (e.g., trigeminal stimulation), delivery of one or more drugs via implanted drug dispensers, cryogenic therapy to the brain tissue, cranial nerves, and/or peripheral nerves), or the like. Similar to vagus nerve stimulation, parameters of the therapy may be constant or the parameters of the therapy may be modified based on the subject's estimated susceptibility.

Such therapies may be used in addition to the vagus nerve stimulation or as an alternative to such therapy. If desired, the type of therapy delivered to the subject may be modified based on the subject's susceptibility. For example, if the elevated susceptibility estimates a long time horizon until seizure and/or a lower confidence level, a more benign type of therapy (e.g., electrical stimulation) may be employed. But if the elevated susceptibility estimates a shorter time horizon until seizure and/or has a higher confidence level, a different type of therapy (e.g., pharmacotherapy) may be employed.

Figure 17:
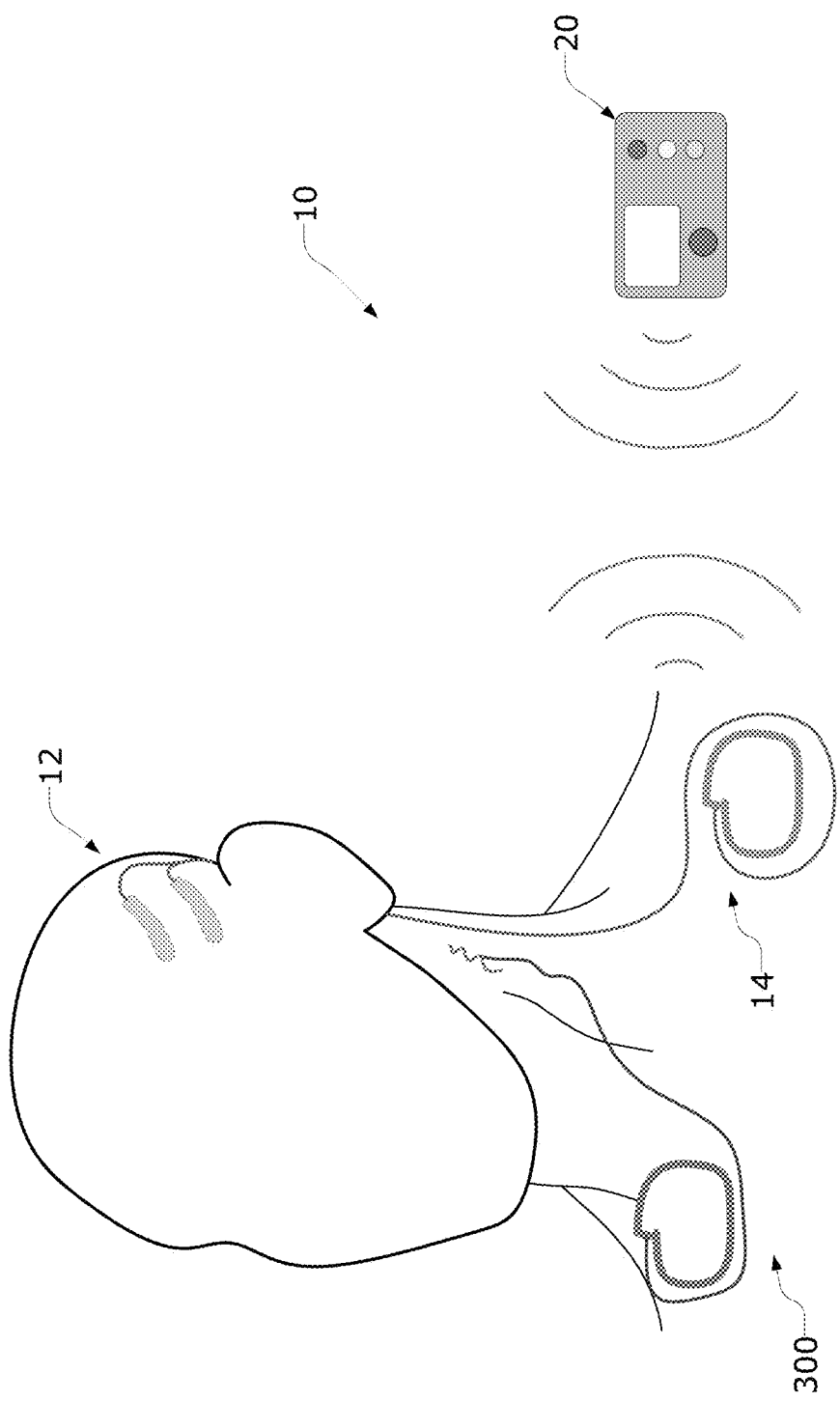
FIG. 17 illustrates a separate vagus nerve stimulator that is used in conjunction with a seizure advisory system.

FIG. 17 illustrates an embodiment of the present invention that is used with an existing open loop Cyberonics vagus nerve stimulator 300. When the system 10 of the present invention determines that the subject is at an elevated risk for a seizure, the system 10 may generate a communication to the subject via the external assembly 20, and the subject may use a wand associated with the vagus nerve stimulator 300 to manually active stimulation of the vagus nerve.

Some embodiments of the monitoring system may include an integral subject diary functionality. The subject diary may be a module in the external assembly and inputs by the subject may be used to provide secondary inputs to provide background information for the sampled EEG signals. For example, if a seizure is recorded, the seizure diary may provide insight regarding a trigger to the seizure, or the like. The diary may automatically record the time and date of the entry by the subject. Entries by the subject may be a voice recording, or through activation of user inputs on the external assembly. The diary may be used to indicate the occurrence of an aura, occurrence of a seizure, the consumption of a meal, missed meal, delayed meal, activities being performed, consumption of alcohol, the subject's sleep state (drowsy, going to sleep, waking up, etc.), mental state (e.g., depressed, excited, stressed), intake of their AEDs, medication changes, missed dosage of medication, menstrual cycle, illness, or the like. Thereafter, the subject inputs recorded in the diary may also be used by the physician in assessing the subject's epilepsy state and/or determine the efficacy of the current treatment. Furthermore, the physician may be able to compare the number of seizures logged by the subject to the number of seizures detected by the seizure detection algorithm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, the present invention also encompasses other more invasive embodiments which may be used to monitor the subject's neurological system.

It is intended that the following claims define the scope of the invention and that methods and structures within the scope of these claims and their equivalents be covered thereby.

What is claimed is:

1. A system for monitoring neurological signals in a patient, the system comprising:
    an implantable sensor adapted to collect neurological signals;
    an implantable assembly configured to sample the neurological signals collected by the sensor, wherein said implantable assembly comprises:
        a physical memory configured to store or buffer said neurological signals;
        a first telemetry circuit;
        a processing subassembly configured to process neurological signals prior to transmission to a rechargeable communication device external to the patient's body; and
    the rechargeable communication device external to the patient's body comprising:
        a display configured to indicate a neurological state of the patient;
        a second telemetry circuit;
        a processor configured to control outputs on the display and manage the second telemetry circuit, at least one of the outputs providing an indication of a change in a brain state of the patient; and
    wherein said rechargeable communication device is configured to wirelessly communicate with the implantable assembly and to transmit a communication error alert to a caregiver advisory device in an event of a communication error between the implantable assembly and the rechargeable communication device, wherein the caregiver advisory device allows at least one of monitoring the patient or facilitating treatment.

2. The system of claim 1, further comprising the caregiver advisory device, wherein the rechargeable communication device is configured to wirelessly communicate with the caregiver advisory device.

3. The system of claim 2, wherein the caregiver advisory device is configured to indicate if there is a communication error between the rechargeable communication device and the implantable assembly.

4. The system of claim 2, wherein the caregiver advisory device is configured to provide a visible alert if there is a communication error between the rechargeable communication device and the implantable assembly.

5. The system of claim 2, wherein the caregiver advisory device is configured to provide an audible alert if there is a communication error between the rechargeable communication device and the implantable assembly.

6. The system of claim 1, wherein the communication error comprises a failure of the rechargeable communication device to receive an expected data signal from the implantable assembly.

7. The system of claim 1, wherein the communication error comprises a failure of the rechargeable communication device to receive a data signal from the implantable assembly for a predetermined amount of time.

8. The system of claim 1, wherein the communication error comprises a failure of the rechargeable communication device to receive a data signal from the implantable assembly at an expected time or within an expected period of time.

9. The system of claim 1, wherein the communication error comprises a missing packet of data in a numbered sequence of packets transmitted from the implantable assembly to the rechargeable communication device.

10. The system of claim 1, wherein the rechargeable communication device is configured to automatically deactivate the communication error alert after a predetermined period of time.

11. The system of claim 1, wherein the implantable sensor is adapted to collect neurological signals from inside the patient's skull.

12. The system of claim 1, wherein the implantable sensor is adapted to collect neurological signals from a location between the patient's skull and at least a layer of the patient's scalp.

13. The system of claim 1, wherein the rechargeable communication device is configured to receive the neurological signals from the implantable assembly.

14. The system of claim 1, wherein the rechargeable communication device is configured to communicate with the caregiver advisory device via a wireless cellular network.

15. The system of claim 1, wherein the rechargeable communication device is configured to communicate with the caregiver advisory device via a phone call.

16. The system of claim 1, wherein the implantable assembly is configured to transmit the neurological signals to the rechargeable communication device substantially immediately after sampling.

17. A method of monitoring neurological signals in a patient, comprising:
    collecting neurological signals using a sensor implanted in the patient;
    sampling the neurological signals using an implantable assembly;

storing or buffering said neurological signals in memory of the implanted assembly;

processing said neurological signals prior to transmission to an external rechargeable communication device using a processor subassembly;

displaying a neurological state of the patient using the rechargeable communication device;

controlling outputs on the rechargeable communication device, at least one of the outputs providing an indication of a change in a brain state of the patient and managing a telemetry circuit using a processor on said rechargeable communication device;

indicating a change in brain state of the patient based on the neurological signals via an output on said rechargeable communication device;

wirelessly transmitting a communication error alert from the rechargeable communication device external to the patient's body to a caregiver advisory device in the event of a communication error between the implantable assembly and the rechargeable communication device wherein the caregiver advisory device allows for at least one of monitoring the patient or facilitating treatment.

18. The method of claim 17, further comprising wirelessly communicating from the rechargeable communication device to the caregiver advisory device.

19. The method of claim 18, further comprising generating an indication from the caregiver advisory device if there is a communication error between the rechargeable communication device and the implantable assembly.

20. The method of claim 18, further comprising providing a visible alert from the caregiver advisory device if there is a communication error between the rechargeable communication device and the implantable assembly.

21. The method of claim 18, further comprising providing a visible alert from the caregiver advisory device if there is a communication error between the rechargeable communication device and the implantable assembly.

22. The method of claim 17, wherein said communication error comprises a failure of the rechargeable communication device to receive an expected data signal from the implantable assembly.

23. The method of claim 17, wherein said communication error comprises a failure of the rechargeable communication device to receive a data signal from the implantable assembly for a predetermined amount of time.

24. The method of claim 17, wherein said communication error comprises a failure of the rechargeable communication device to receive a data signal from the implantable assembly at an expected time or within an expected period of time.

25. The method of claim 17, wherein said communication error comprises a missing packet of data in a numbered sequence of packets transmitted from the implantable assembly to the rechargeable communication device.

26. The method of claim 17, further comprising automatically deactivating the communication error alert after a predetermined period of time.

27. The method of claim 17, wherein said collecting neurological signals comprises collecting neurological signals from inside the patient's skull.

28. The method of claim 17, wherein said collecting neurological signals comprises collecting neurological signals from a location between the patient's skull and at least a layer of the patient's scalp.

29. The method of claim 17, further comprising receiving at the rechargeable communication device the neurological signals from the implantable assembly.

30. The method of claim 17, wherein said transmitting the communication error alert comprises transmitting the communication error alert from the rechargeable communication device to the caregiver advisory device via a wireless cellular network.

31. The method of claim 17, wherein said transmitting the communication error alert comprises transmitting the communication error alert from the rechargeable communication device to the caregiver advisory device via a phone call.

32. The method of claim 17, further comprising transmitting the neurological signals from the implantable assembly to the rechargeable communication device substantially immediately after sampling.

* * * * *